(12) United States Patent
Little et al.

(10) Patent No.: US 8,496,835 B2
(45) Date of Patent: Jul. 30, 2013

(54) ANION-EXCHANGE DISPLACEMENT CHROMATOGRAPHY PROCESS AND ANIONIC ORGANIC COMPOUNDS FOR USE AS DISPLACER COMPOUNDS IN ANION-EXCHANGE DISPLACEMENT CHROMATOGRAPHY PROCESS

(75) Inventors: Charles Little, Austin, TX (US); Barry L. Haymore, Austin, TX (US)

(73) Assignee: Sachem, Inc., Austin, TX (US)

( * ) Notice: Subject to any disclaimer, the term of this patent is extended or adjusted under 35 U.S.C. 154(b) by 1067 days.

(21) Appl. No.: 11/564,951

(22) Filed: Nov. 30, 2006

(65) Prior Publication Data

US 2007/0125712 A1 Jun. 7, 2007

Related U.S. Application Data

(60) Provisional application No. 60/741,863, filed on Dec. 2, 2005.

(51) Int. Cl.
*B01D 15/08* (2006.01)
*C02F 1/28* (2006.01)
*G01N 30/02* (2006.01)

(52) U.S. Cl.
USPC .......................... 210/656; 210/198.2; 422/70

(58) Field of Classification Search
USPC .............................................. 210/198.2, 656
See application file for complete search history.

(56) References Cited

U.S. PATENT DOCUMENTS

| 5,028,696 | A | 7/1991 | Torres et al. |
| 5,346,984 | A | 9/1994 | Hasegawa et al. |
| 5,439,591 | A | 8/1995 | Pliura et al. |
| 5,478,924 | A | 12/1995 | Cramer |
| 5,545,328 | A | 8/1996 | Pliura et al. |
| 5,606,033 | A | 2/1997 | Cramer et al. |
| 6,239,262 | B1 | 5/2001 | Cramer et al. |
| 6,245,238 | B1 | 6/2001 | Agner |

(Continued)

FOREIGN PATENT DOCUMENTS

FR 2779955 12/1999

OTHER PUBLICATIONS

Belgorodsky et al., "β-lactoglobulin as a versatile vehicle for various ligands—Mapping of the elusive binding sites". Meeting Abstracts—Electrochemcal Society. vol. 801 (2008), p. 953.*
http://www.sigmaaldrich.com/technical-service-home/product-catalog.html, accessed Nov. 26, 2008, 1 page.*
Kundu et al. Displacement chromatography of proteins using low molecular weight anionic displacers. Adsorption 4, 373-381 (1998).*
Partial International Search Report, Application No. PCT/US2006/045872, dated May 21, 2007.

*Primary Examiner* — Katherine Zalasky
(74) *Attorney, Agent, or Firm* — Renner, Otto, Boisselle & Sklar, LLP

(57) ABSTRACT

A displacement chromatography process, including: loading onto a stationary phase comprising an anion-exchange material a mixture comprising one or more components to be separated; and displacing at least one of the one or more components from the stationary phase by applying to the stationary phase a mixture comprising an polyaromatic polyanionic displacer compound having a general formula $Cen(Ar)_w$, in which Cen is a central bond or group, Ar is an aromatic nucleus, w=2 to the maximum number of sites one Cen, and Ar is substituted with a plurality of $An^-$, in which each $An^-$ is independently defined as sulfonate, carboxylate, phosphonate, phosphate, sulfate; and Ar is further substituted with a plurality of G, in which G is defined as independently H, $C_1$-$C_6$ alkyl, halogen, nitro, hydroxy, or $C_1$-$C_6$ alkoxy. In addition, a group of polyaromatic polyanionic displacer compounds useful in the process is disclosed.

46 Claims, 3 Drawing Sheets

U.S. PATENT DOCUMENTS

| | | |
|---|---|---|
| 6,573,373 B1 | 6/2003 | Shukla et al. |
| 6,576,134 B1 | 6/2003 | Agner |
| 6,828,436 B2 | 12/2004 | Shukla et al. |
| 6,929,747 B2 | 8/2005 | Cramer et al. |

* cited by examiner

ANION-EXCHANGE DISPLACEMENT CHROMATOGRAPHY PROCESS AND ANIONIC ORGANIC COMPOUNDS FOR USE AS DISPLACER COMPOUNDS IN ANION-EXCHANGE DISPLACEMENT CHROMATOGRAPHY PROCESS

CROSS-REFERENCE TO RELATED APPLICATION

The present application is related to and claims benefit under 35 U.S.C. §119(e) to U.S. Provisional Application No. 60/741,863, filed 2 Dec. 2005, the entirety of which is incorporated by reference.

TECHNICAL FIELD

The present invention pertains to compositions comprising multiple organic anion salts (multiple anions), and processes of using said compositions as displacers in anion-exchange displacement chromatographic purifications.

BACKGROUND

The displacement mode of chromatography was first recognized in 1906 by Tswett, who noted that sample displacement occurred under conditions of overloaded elution chromatography. In 1943, Tiselius proposed that the broad subject of chromatography could be organized around three distinct "modes:" frontal mode, elution mode, and displacement mode. Since then, most developments and applications, particularly those in analytical chromatography, have taken place in the area of elution chromatography. Indeed, the term "chromatography" without further qualification today usually refers to chromatography in the elution mode.

Elution mode and displacement mode are readily distinguished both in theory and in practice. In elution chromatography, a solution of the sample to be purified is applied to a stationary phase, commonly in a column. The mobile phase is chosen such that the sample is neither irreversibly adsorbed nor totally non-adsorbed, but rather binds reversibly. As the mobile phase is flowed over the stationary phase, an equilibrium is established between the mobile phase and the stationary phase whereby, depending upon the affinity for the stationary phase, the sample passes along the column at a speed which reflects its affinity relative to other components that may be present in the original sample. Of particular note in standard elution chromatography is the fact that the eluting solvent front, or zero column volume in isocratic elution, always precedes the sample off the column.

A modification and extension of isocratic elution chromatography is found in step gradient chromatography wherein a series of eluents of varying composition are passed over the stationary phase. In ion-exchange chromatography, for example, step changes in the mobile phase salt concentration and/or pH are employed to elute or desorb analytes undergoing separation.

Displacement chromatography employs a displacer compound to remove components of a mixture from the column. The displacer compound generally has a much higher affinity for the stationary phase than do any of the components in the mixture to be separated. This is in contrast to elution chromatography, where the eluent has a lower affinity for the stationary phase than do the components to be separated. A key operational feature that distinguishes displacement chromatography from elution or desorption chromatography is the use of a displacer compound. In displacement chromatography, the column is first equilibrated with a carrier solvent under conditions in which the components to be separated all have a relatively high affinity for the stationary phase. A volume of feed mixture, which can be large and quite dilute, is loaded onto the column and individual components in the feed mixture will adsorb to the stationary phase. That is, the components of the feed mixture are distributed and adsorbed onto the stationary phase, and remain there. If all the components are to be resolved by displacement, the carrier solvent emerges from the column containing no sample. The components of the feed mixture now reside on the stationary phase, and the position of each component on the column is correlated with its relative affinity for the stationary phase under the initial conditions. In principle, a molecule of any component will displace a molecule of any different component having a lower affinity at a given site on the stationary phase. As a result, individual components will ultimately be arranged on the column in sequence from highest to lowest affinity.

It is sometimes advantageous to allow some components of the feed mixture, e.g., components not having a significant affinity for the stationary phase, to pass through the column with the carrier solvent; in this case only the retained feed components will be resolved by displacement chromatography.

Once the sample is loaded on the column, a solution containing a displacer compound in a suitable solvent is introduced into the column to pass through the stationary phase. The displacer compound is selected such that it has a higher affinity for the stationary phase than do any of the components of the feed mixture. Assuming that the displacer and mobile phase are appropriately chosen, the individual components exit the column as adjacent zones of highly concentrated, relatively pure material in the order of increasing affinity of absorption. Following the zones of the purified individual components, the displacer emerges from the column. A displacement chromatogram is readily distinguished from an elution chromatogram by virtue of the fact that the displacer compound follows the sample and that the feed components exit the column as adjacent zones of highly concentrated, relatively pure material.

Displacement chromatography has some particularly advantageous characteristics for process scale chromatography. First, displacement chromatography can achieve product separation and concentration in a single step. By comparison, isocratic elution chromatography results in significant product dilution during separation. Second, since the displacement process operates in the nonlinear region of the equilibrium isotherm, high column loadings are possible. This allows much better column utilization than elution chromatography. Third, column development and component separation requires less solvent than a comparable elution process. Fourth, displacement chromatography can concentrate and purify components from mixtures having low separation factors, while relatively large separation factors are required for satisfactory resolution in typical elution chromatography.

With all of these advantages, one might presume that displacement chromatography would be widely utilized. However, problems have persisted in displacement chromatography. One such problem is the need to regenerate the column, since it would not be economical to discard the stationary phase after each use. Another such problem is obtaining suitable displacer compounds that are relatively simple compounds, easily synthesized and/or commercially available at a reasonable (economical) cost. These two problems have presented significant drawbacks to displacement chromatography vis-a-vis elution chromatography.

With respect to regeneration, since the displacement process uses a displacer compound having a very high affinity for the stationary phase, the time needed to regenerate and re-equilibrate the column can be long compared to elution chromatography. Furthermore, relatively large amounts of solvent are often required during regeneration. These problems have effectively reduced the advantages of displacement chromatography over elution chromatography.

The second problem, that of obtaining useful displacer compounds that can be synthesized relatively easily and/or that are commercially available at a reasonable (economical) cost, is due to the need for a displacer compound that has both a high affinity for the stationary phase but that can also be relatively easily removed from the column during regeneration. Such compounds that have been offered by the prior art do not meet one or both of these two important criteria. Various compounds have been offered as low molecular weight displacers, but these have been quite difficult to synthesize and purify and have not been commercially available at reasonable cost, or simply not commercially available.

In order for displacement chromatography to become a mainstream chromatographic technique, there remains a significant unmet need for effective displacers whose synthesis and purification are straightforward and that are amenable to large-scale production, and/or that are commercially available, and which allow for efficient regeneration of the stationary phase so that the stationary phase can be subsequently reused in displacement chromatography processes.

SUMMARY

It has now been found that certain negatively charged organic compounds of low molecular weight can function very efficiently as displacer compounds in a displacement chromatography process. Thus, the present invention relates to both a displacement chromatography process and a group of anionic displacer compounds. The anionic displacer compounds in accordance with the present invention may be efficiently removed from the stationary phase after being used as the displacer compound in a displacement chromatography process, allowing for regeneration and re-use of the stationary phase in subsequent displacement chromatography processes. Furthermore, these anionic displacer compounds can be made in good yield and in high purity, by relatively straightforward and inexpensive synthetic methods. Thus, the present invention addresses the aforementioned problems in displacement chromatography processes of the prior art.

In one embodiment, the present invention includes aromatic polyanionic compounds as the organic displacer compound. In one embodiment, the aromatic polyanionic compounds include polyaromatic polyanionic compounds. In one embodiment, the polyaromatic polyanionic compounds have a low molecular weight. In one embodiment, the polyaromatic polyanionic compounds are novel compounds in themselves, as well as being novel displacer compounds for displacement chromatography processes.

In one embodiment, the present invention relates to displacer compositions comprising one or more of the displacer compounds described herein.

In one embodiment, the present invention relates to a polyaromatic polyanionic displacer compound having the general formula:

$$Cen(Ar)_w$$

wherein Cen=a bond, an alkenyl group, an alkynyl group, a benzene ring, a biphenylene, a naphthylene, or

[chemical structure] or [chemical structure]

wherein:
R=independently —H, $C_1$-$C_4$ alkyl, or $C_1$-$C_4$ hydroxyalkyl;
Z=independently —H, halogen, —OH, —OR, —NRCH$_2$CH(OH)CH$_2$OH, —NR$_2$, —N[CH$_2$CH(OH)CH$_2$OH]$_2$, —NRC(CH$_2$OH)$_3$, —NRCH(CH$_2$OH)$_2$, or —N(R)(poly(alkylene oxide));
w=2 to the highest number of substitutable positions on Cen; and
Ar=(a), (b) and/or (c); and wherein, in the following (a), (b) and (c):
An$^-$=independently sulfonate, carboxylate, phosphonate, phosphinate, phosphate, a phosphate mono- or di-ester, sulfate, a sulfate mono-ester; or boronate;
G=independently H, $C_1$-$C_6$ alkyl, $C_1$-$C_6$ alkenyl, $C_6$-$C_{10}$ aryl, halogen, nitro, hydroxy, $C_1$-$C_6$ alkoxy, cyano, —NH$_2$, —NRH, —NR$_2$, —NHC(O)R, —CHO, —C(O)R; and
(a), (b) and (c) are:

(a) Ar = [chemical structure with $(An^-)_x$ and $(G)_y$]

wherein in (a):
x = 1-3
y = 2-4
x + y = 5; and/or (b) Ar = [chemical structure with $(An^-)_x$ and $(G)_y$] or [chemical structure with $(An^-)_x$ and $(G)_y$]

wherein in either (b):
x = 1-3
y = 4-6
x + y = 7; and/or

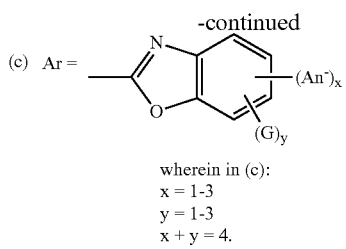

(c) Ar = wherein in (c):
x = 1-3
y = 1-3
x + y = 4.

In one embodiment, any two or more of the Ar groups may be bonded to each other in addition to the bond to Cen. In such an embodiment, G constitutes a bond to another Ar group.

In one embodiment, the polyaromatic polyanionic displacer compound includes a combination of two or more of (a), (b) or (c) as Ar groups attached to Cen. As defined above, each An$^-$, each G, each R and each Z may be selected independently of every other An$^-$, G, R and Z in any given compound. The line or bond extending from the various Cen and Ar moieties represents the bond between each Ar and the Cen to which it is attached.

In one embodiment, the present invention relates to a displacement chromatography process, comprising:

loading onto a suitable stationary phase a mixture comprising at least one component to be separated;

displacing said at least one component from the stationary phase by applying to the stationary phase a mixture comprising an anionic displacer compound comprising a polyaromatic polyanionic compound having the general formula Cen (Ar)$_w$, wherein Cen, Ar, w and the substituents thereon and other variables are defined as above for the polyaromatic polyanionic compounds described above.

Thus, the present invention provides anionic displacer compounds, compositions and processes for displacement chromatography which addresses the need for effective anionic displacer compounds whose synthesis and purification are straightforward and amenable to large-scale production, which allow for efficient regeneration of the stationary phase so that the stationary phase may be reused efficiently.

Figure 1:
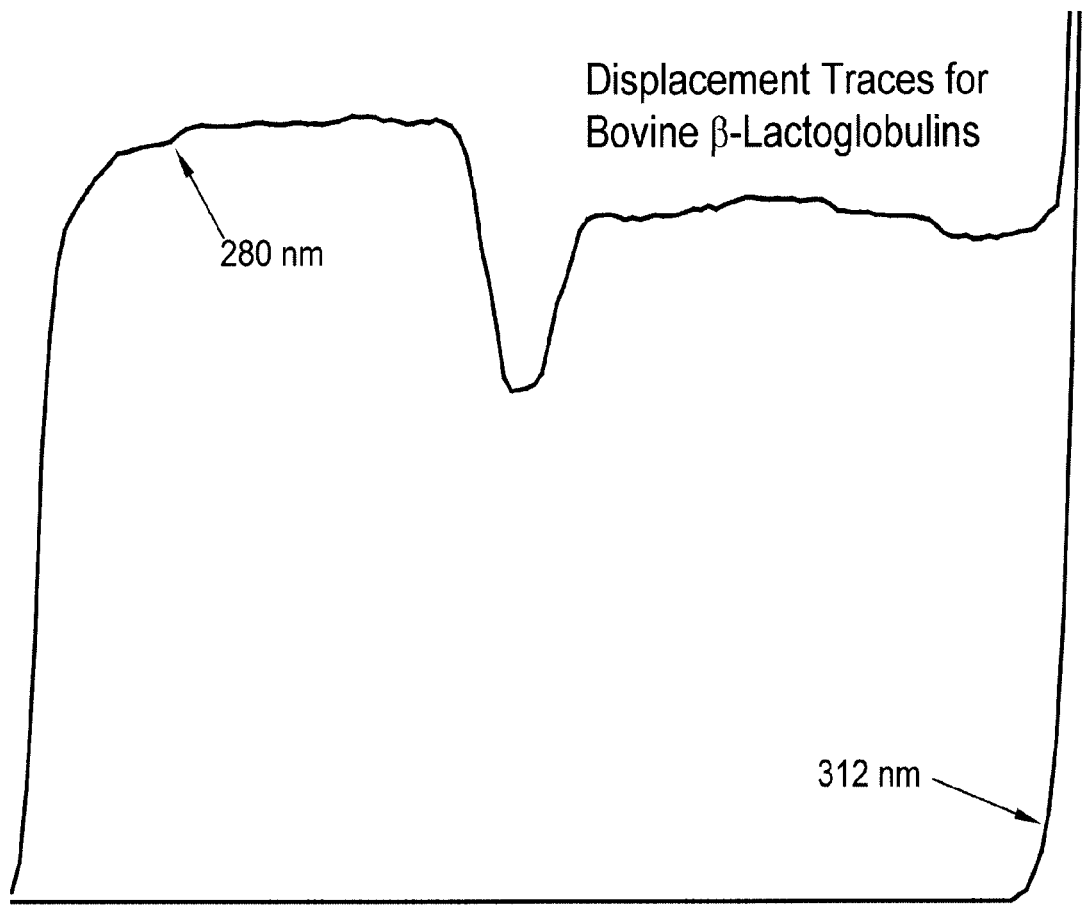
FIG. 1 is a graph depicting the output of a UV/Vis HPLC detector at various wavelengths during displacement chromatography of a mixture of bovine β-lactoglobulin A and bovine β-lactoglobulin B, in accordance with an embodiment of the invention.

It should be appreciated that the process steps and compositions described herein may not form a complete system or process flow for carrying out a displacement chromatography process, such as would be used in actual practice. The present invention can be practiced in conjunction with synthetic organic and displacement chromatography techniques and apparatus currently used in the art, and only so much of the commonly practiced materials, apparatus and process steps are included as are necessary for an understanding of the present invention.

DETAILED DESCRIPTION

As used herein "halo" refers to a group comprising a halogen, such as chloro, bromo, fluoro, or iodo.

As used herein, "alkyl" and "alkylene" refer to a group of carbon and hydrogen atoms derived from an alkane molecule by removing one or two hydrogen atoms, as appropriate. "Alkyl" and "alkylene" may include saturated monovalent and divalent hydrocarbon radicals having straight, cyclic or branched moieties. The "alkyl" or "alkylene" groups may include an optional carbon-carbon double or triple bond where said alkyl group comprises at least two carbon atoms. It is understood that for cyclic moieties at least three carbon atoms are required in said alkyl group. In the present invention, alkyl and alkylene groups may include any number of carbon atoms. In one embodiment of the present invention, about 20 or less carbon atoms may be used. For example, in one embodiment, alkyl groups of 2, 3, 4, 5, 6, 7, 8, 9, 10, 11, 12, 13, 14, 15, 16, 17, 18, 19, or 20 carbons may be employed in the present invention. Of course, alkyl groups of longer length or branched may be employed in the present invention. Alkylene groups may be used, for example, in an embodiment in which a ring is to be formed from two groups that would otherwise be alkyl groups.

As used herein, "aryl" refers to an unsubstituted or substituted aromatic structure such as phenyl, naphthyl, fluorenyl, phenanthryl, etc. The aryl group, when substituted, may be substituted by a halo group, an alkyl group, another aryl group or an aralkyl group, as defined herein.

As used herein, "aralkyl" refers to a radical in which an aryl group is substituted for a hydrogen atom of an alkyl group. "Aryl" is as defined above. In the present invention, aralkyl groups may include any number of carbon atoms. In one embodiment of the present invention, the aralkyl group contains about 20 or less carbon atoms. For example, in one embodiment, aralkyl groups of 7, 8, 9, 10, 11, 12, 13, 14, 15, 16, 17, 18, 19, or 20 carbons may be employed in the present invention. Of course, aralkyl groups of more carbon atoms may be employed in the present invention.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 and the like, are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Aromatic Anionic Displacer Compounds

In one embodiment, the present invention relates to a polyaromatic polyanionic displacer compound having the general formula:

Cen(Ar)$_w$ wherein Cen=a bond, an alkenyl group, an alkynyl group, a benzene ring, a biphenylene, a naphthylene, or

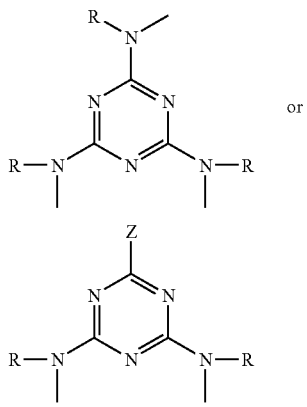

wherein:

R=independently —H, $C_1$-$C_4$ alkyl, or $C_1$-$C_4$ hydroxyalkyl;

Z=independently —H, halogen, —OH, —OR, —NRCH$_2$CH(OH)CH$_2$OH, —NR$_2$, —N[CH$_2$CH(OH)CH$_2$OH]$_2$, —NRC(CH$_2$OH)$_3$, —NRCH(CH$_2$OH)$_2$, or —N(R)(poly(alkylene oxide));

w=2 to the highest number of substitutable positions on Cen; and

Ar=(a), (b) and/or (c); and wherein, in the following (a), (b) and (c):

An$^-$=independently sulfonate, carboxylate, phosphonate, phosphinate, phosphate, a phosphate mono- or di-ester, sulfate, a sulfate mono-ester; or boronate;

G=independently H, $C_1$-$C_6$ alkyl, $C_1$-$C_6$ alkenyl, $C_6$-$C_{10}$ aryl, halogen, nitro, hydroxy, $C_1$-$C_6$ alkoxy, cyano, —NH$_2$, —NRH, —NR$_2$, —NHC(O)R, —CHO, —C(O)R; and (a), (b) and (c) are:

(a)

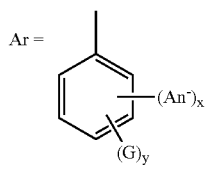

wherein in (a):
x = 1-3
y = 2-4
x+y = 5; and/or (b)

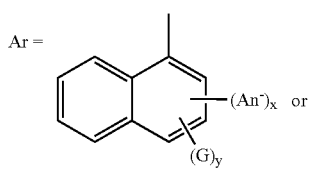

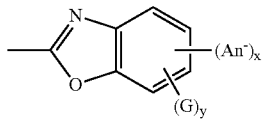

wherein in either (b):
x = 1-3
y = 4-6
x+y = 7; and/or (c)

Ar =

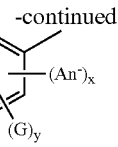

wherein in (c):
x = 1-3
y = 1-3
x+y = 4.

In one embodiment, any two or more of the Ar groups may be bonded to each other in addition to the bond to Cen. In such an embodiment, G constitutes a bond to another Ar group.

In one embodiment, the polyaromatic polyanionic displacer compound includes a combination of two or more of (a), (b) or (c) as Ar groups attached to Cen. As defined above, each An$^-$, each G, each R and each Z may be selected independently of every other An$^-$, G, R and Z in any given compound. The line or bond extending from the various Cen and Ar moieties represents the bond between each Ar and the Cen to which it is attached.

The polyaromatic polyanionic displacer compounds in accordance with the present invention belong to a class of compounds known as aromatic polyanions, which may be acids or salts or aromatic polyanionic compounds, in which the compounds have two or more aromatic nuclei on which are carried a plurality of anionic moieties. The polyaromatic polyanionic compounds of the present invention are generally polyacids that when dissociated form a plurality of negatively charged groups (polyanions). In the present disclosure, the structures are generally shown in their respective acid forms. As will be understood, in the pH range at which the polyaromatic polyanionic displacer compounds of the present invention are used, these compounds will be dissociated into the anionic form to some degree. That is, in general, relatively strongly acidic groups such as sulfonates usually will be fully dissociated, while less strongly acidic groups such as carboxylates may not be fully dissociated. As is known in the art, the degree of dissociation at a given pH depends on the pK of the compound. The acid forms of the compounds are shown herein for uniformity and convenience, and it is not intended that such compounds are necessarily in the acid form.

In one embodiment, the polyaromatic polyanionic compounds in accordance with the present invention comprise a plurality of negatively-charged atoms. In one embodiment, the anionic organic compound may comprise more than one type of anionic moiety. In one embodiment, the anionic moiety may be one or more of carboxylate, sulfonate, phosphonate, sulfate and phosphate, and is generally represented by An$^-$. In any given embodiment of the aromatic anionic compound, a plurality of any one of these An$^-$ moieties may be present, or a mixture of one or more each of any two or more of these An$^-$ moieties may be present. In many embodiments, the anionic moieties An$^-$ in a given aromatic anionic compound are all the same, but in other embodiments, there is a mixture or combination of two or more such anionic moieties An⁻. Thus, for example, there may be a combination of sulfonate and carboxylate groups.

In one embodiment, the polyaromatic polyanionic compounds in accordance with the present invention carry a plurality of anionic moieties on a plurality of aromatic nuclei. That is, in an embodiment in which there are multiple aromatic nuclei, each of the plurality of aromatic nuclei carries a plurality of anionic moieties. In one embodiment, one or more aromatic nuclei carry no anionic moiety. For example, in some embodiments, an aromatic nuclei is the central, linking group to which a plurality of anionic moiety-carrying aromatic nuclei are attached.

In one embodiment, the anionic organic compounds comprise a plurality of aromatic nuclei on each of which a plurality of anionic groups are identically distributed on each of the plurality of aromatic nuclei. That is, in an embodiment in which there are multiple aromatic nuclei, in which a plurality of the aromatic nuclei are substituted, the anionic moieties are attached at the same position of each aromatic nucleus. For example, two benzene nuclei (phenyl groups) each may be attached to the remainder of the anionic organic compound at the 1-position of each ring, and two sulfonate groups are attached to each ring at the 3 and 5 position.

In one embodiment, the anionic organic compounds comprise a plurality of aromatic nuclei on each of which a plurality of anionic groups are identically distributed on each of the plurality of aromatic nuclei, and in which the anionic organic compound as a whole exhibits at least one axis of symmetry. That is, in an embodiment in which there are multiple aromatic nuclei, in which a plurality of the aromatic nuclei are substituted, the anionic moieties are attached at the same position of each aromatic nucleus and the molecule as a whole exhibits at least one axis of symmetry. For example, two benzene nuclei each may be attached to the other at the 1-position of each ring, and two sulfonate groups are attached to each ring at the 3 and 5 position. This molecule has bilateral symmetry, each side of the molecule being a mirror image of the other.

In one embodiment, the aromatic nuclei Ar, which may be substituted or unsubstituted, include in addition to the groups described above, various heterocyclic aromatics, including, but not limited to, benzofuran, isobenzofuran, benzotriazole, benzothiazole, benzo[b]thiophene, benzo[c]thiophene, indole, benzimidazole, cinnoline, quinazoline, naphthyridine, pyrido[3,4-b]-pyridine, pyrido[3,2-b]-pyridine, pyrido[4,3-b]-pyridine, quinoline, isoquinoline, phenothiazine, acridine, benzisooxazole, anthranil, and polyaromatic groups such as anthracene and phenanthrene.

When substituted, the aromatic nuclei Ar may be substituted with any of the G groups as defined above, consistent with the An⁻ substituents also present.

In one embodiment, the anionic organic compounds are water soluble. When soluble in water, these compounds exhibit the useful property of having a plurality of negative charges that are spread out, often in a uniform pattern.

In one embodiment, the present invention includes aromatic polyanionic compounds as the organic displacer compound. In one embodiment, the aromatic polyanionic compounds include polyaromatic polyanionic compounds as described in more detail herein. In one embodiment, the aromatic polyanionic compounds have a low molecular weight. In one embodiment, the aromatic polyanionic compounds are novel compounds in themselves, as well as being novel displacer compounds for displacement chromatography processes.

In the following, various examples are provided of compounds having the general formula Cen(Ar)w, as defined above. These examples are not meant to be limiting, but are provided to illustrate some of the possible embodiments of the present invention.

In one embodiment, the polyaromatic polyanionic compound has the following general formula (I):

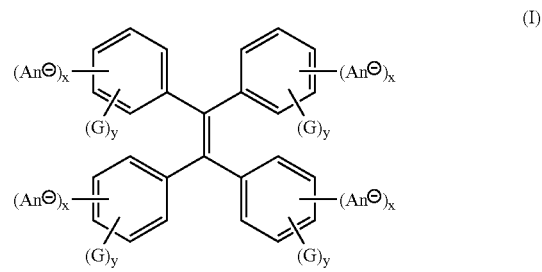

(I)

wherein in (I), each An⁻, each G, each x and each y may be selected independently from the above definitions. In one embodiment, in each molecule (I), each An⁻ is the same on each Ar nucleus, and in another embodiment, one or more An⁻ differs from other An⁻ groups. In one embodiment, in each molecule (I), the value of each x is the same on each Ar nucleus as the value of x on each other Ar nucleus, and in another embodiment, one or more value of x differs from other values of x. In one embodiment, in each molecule (I), each G is the same on each Ar nucleus, and in another embodiment, one or more G differs from other G. In one embodiment, in each molecule (I), each value of y is the same on each Ar nucleus as the value of y on each other Ar nucleus, and in another embodiment, one or more value of y is different from other values of y. In one embodiment, the An⁻ groups are symmetrically arranged on the Ar nuclei. In one embodiment, the G groups are arranged symmetrically on the Ar nuclei. In one embodiment, the molecule as a whole has at least one axis of symmetry.

In one embodiment, the aromatic polyanionic compound having the general structure (I) is a compound such as the following aromatic polyanionic compound having the general formula (I-A) which may be conveniently referred to as AD1 (anionic displacer 1):

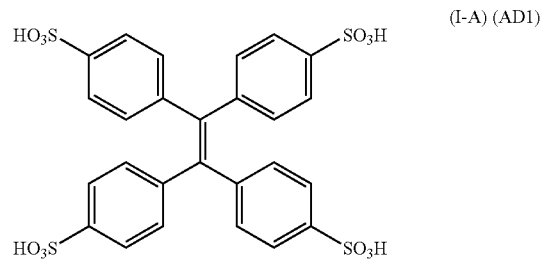

(I-A) (AD1)

In this embodiment of compound (I), An⁻ is sulfonate in all cases, x=1 in all cases and the sulfonate is on the 4-position (para) of each aromatic nucleus. A synthesis of compound (I-A) is described in Example 1, and use of compound (I-A) in a displacement chromatography procedure is described in Example 3.

In one embodiment, the polyaromatic polyanionic compound has the following general structure (II):

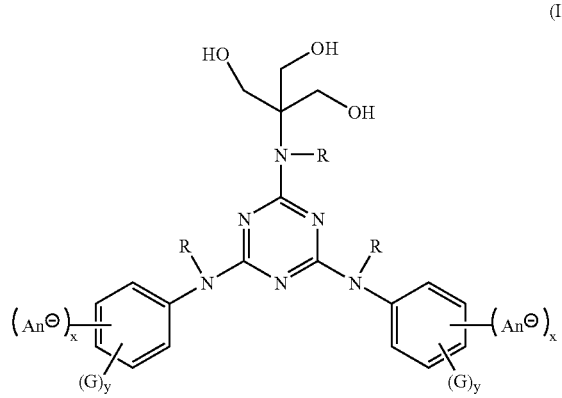

(II)

wherein in (II), each An⁻, each G, each R, each x and each y may be selected independently from the above definitions. In one embodiment, in each molecule (II), each An⁻ is the same on each Ar nucleus, and in another embodiment, one or more An⁻ differs from other An⁻ groups. In one embodiment, in each molecule (II), the value of each x is the same on each Ar nucleus as the value of x on each other Ar nucleus and in another embodiment, one or more value of x differs from other values of x. In one embodiment, in each molecule (II), each G is the same on each Ar nucleus, and in another embodiment, one or more G differs from other G. In one embodiment, in each molecule (II), each value of y is the same on each Ar nucleus as the value of y on each other Ar nucleus, and in another embodiment, one or more value of y is different from other values of y. In one embodiment, in each molecule (II), each R is the same on each N, and in another embodiment, one or more R differs from other R on other N. In one embodiment, the An⁻ groups are symmetrically arranged on the Ar nuclei. In one embodiment, the G groups are arranged symmetrically on the Ar nuclei. In one embodiment, the molecule as a whole has at least one axis of symmetry.

In one embodiment, the aromatic polyanionic compound having the general structure (II) is a compound such as the following aromatic polyanionic compound having the general formula (II-A) which may be conveniently referred to as AD2, and has the following structure:

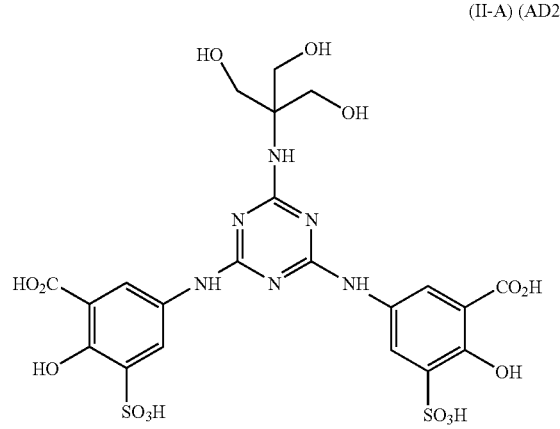

(II-A) (AD2)

in (II-A), x=2 in each phenyl group, in each phenyl group the two An⁻ groups are different, one An⁻ represents a sulfonate and one An⁻ represents a carboxylate and the two An⁻ groups are in the 3 and 5 (meta) positions on the phenyl groups.

In one embodiment, the polyaromatic polyanionic compound has the following general structure (III):

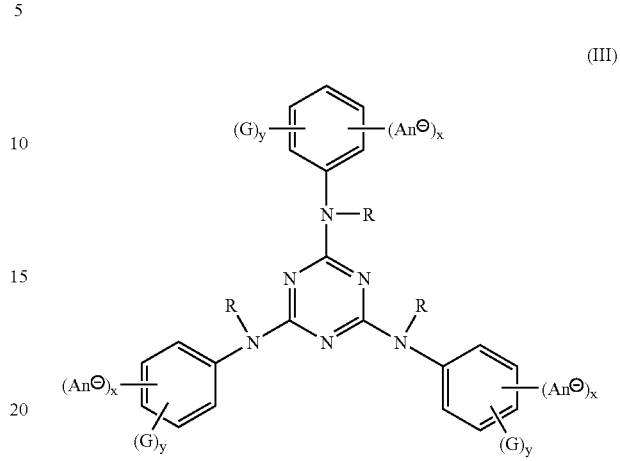

(III)

wherein in (III), each An⁻, each G, each R, each x and each y may be selected independently from the above definitions. In one embodiment, in each molecule (III), each An⁻ is the same on each Ar nucleus, and in another embodiment, one or more An⁻ differs from other An⁻ groups. In one embodiment, in each molecule (III), each value of x is the same on each Ar nucleus as the value of x on each other Ar nucleus and in another embodiment, one or more value of x differs from other values of x. In one embodiment, in each molecule (III), each G is the same on each Ar nucleus, and in another embodiment, one or more G differs from other G. In one embodiment, in each molecule (III), each value of y is the same on each Ar nucleus as the value of y on each other Ar nucleus, and in another embodiment, one or more value of y is different from other values of y. In one embodiment, in each molecule (III), each R is the same on each N, and in another embodiment, one or more R differs from other R on other N. In one embodiment, the An⁻ groups are symmetrically arranged on the Ar nuclei. In one embodiment, the G groups are arranged symmetrically on the Ar nuclei. In one embodiment, the molecule as a whole has at least one axis of symmetry.

In one embodiment, the aromatic polyanionic compound having the general structure (III) is a compound such as the following aromatic polyanionic compound having the general formula (III-A) having the following structure:

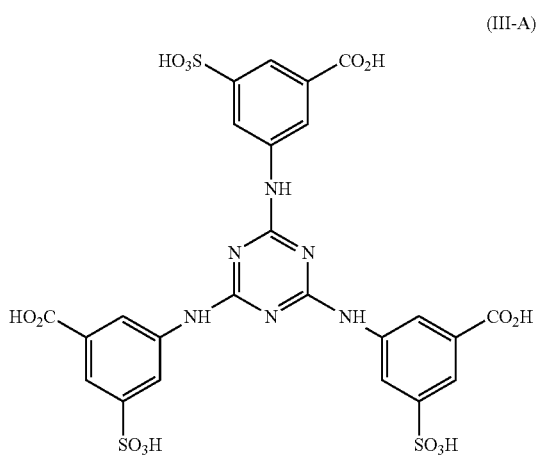

(III-A)

In one embodiment, the aromatic polyanionic compound having the general structure (III) is a compound such as the following aromatic polyanionic compound having the general formula (III-B) which may be referred to as AD-4 and has the following structure:

(III-B) (AD4)

In one embodiment, the polyaromatic polyanionic compound has the following general structure (IV):

(IV)

wherein in (IV), each $An^-$, each G, each x and each y may be selected independently from the above definitions. In one embodiment, in each molecule (IV), each $An^-$ is the same on each Ar nucleus, and in another embodiment, one or more $An^-$ differs from other $An^-$ groups. In one embodiment, in each molecule (IV), each value of x is the same on each Ar nucleus as the value of x on each other Ar nucleus, and in another embodiment, one or more value of x differs from other values of x. In one embodiment, in each molecule (IV), each G is the same on each Ar nucleus, and in another embodiment, one or more G differs from other G. In one embodiment, in each molecule (IV), each value of y is the same on each Ar nucleus as the value of y on each other Ar nucleus, and in another embodiment, one or more value of y is different from other values of y. In one embodiment, the $An^-$ groups are symmetrically arranged on the Ar nuclei. In one embodiment, the G groups are arranged symmetrically on the Ar nuclei. In one embodiment, the molecule as a whole has at least one axis of symmetry.

In one embodiment, the polyaromatic polyanionic compound (IV) has one of the two following structures, (IV-A) or (IV-B), which may be conveniently referred to as AD5 and AD6, respectively.

(IV-A) (AD5)

(IV-B) (AD6)

In another embodiment, the polyaromatic polyanionic compound (IV) has the following structure (IV-C):

(IV-C)

In all of (IV-A), (IV-B) and (IV-C), the substituents have the definitions provided above for the structure (IV). In one embodiment, the compounds having structure (IV-C) are one or more of the exemplary compounds, or isomers or congeners of, those compounds shown in FIG. 3. The congeners of the compounds include, for example, alkyl groups, alkoxy groups and halogens included within those described above with respect to the compound having the general structure (IV). Thus, in addition to the specific compounds shown in FIG. 3, any other compound within the scope of the general structure (IV) is included within this definition. It is noted that the above compound (IV-B) or AD-6 corresponds to structure (I) in FIG. 3.

In one embodiment, the polyaromatic polyanionic compound has the following general structure (V):

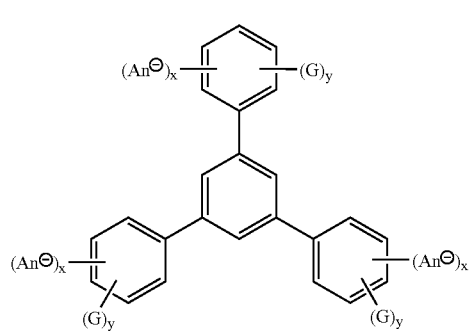

(V)

wherein in (V), each An⁻, each G, each x and each y may be selected independently from the above definitions. In one embodiment, in each molecule (V), each An⁻ is the same on each Ar nucleus, and in another embodiment, one or more An⁻ differs from other An⁻ groups. In one embodiment, in each molecule (V), each value of x is the same on each Ar nucleus as the value of x on each other Ar nucleus, and in another embodiment, one or more value of x differs from other values of x. In one embodiment, in each molecule (V), each G is the same on each Ar nucleus, and in another embodiment, one or more G differs from other G. In one embodiment, in each molecule (V), each value of y is the same on each Ar nucleus as the value of y on each other Ar nucleus, and in another embodiment, one or more value of y is different from other values of y. In one embodiment, the An⁻ groups are symmetrically arranged on the Ar nuclei. In one embodiment, the G groups are arranged symmetrically on the Ar nuclei. In one embodiment, the molecule as a whole has at least one axis of symmetry.

In one embodiment, the aromatic polyanionic compound having the general structure (V) is a compound such as the following aromatic polyanionic compound having the general formula (V-A) which may be conveniently referred to as AD3, and has the following structure:

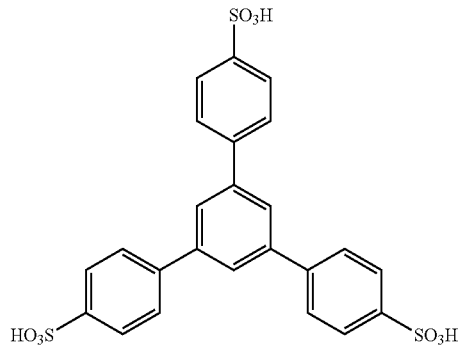

(V-A) (AD3)

In one embodiment, the polyaromatic polyanionic compound has the following general structure (VI):

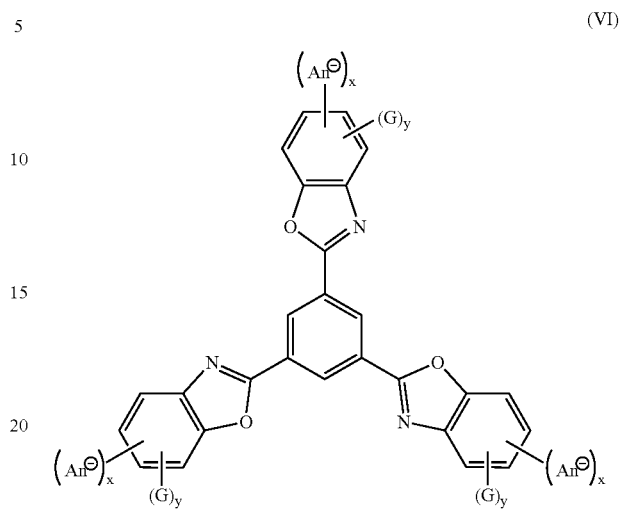

(VI)

wherein in (VI), each An⁻, each G, each x and each y may be selected independently from the above definitions. In one embodiment, in each molecule (VI), each An⁻ is the same on each Ar nucleus, and in another embodiment, one or more An⁻ differs from other An⁻ groups. In one embodiment, in each molecule (VI), each value of x is the same on each Ar nucleus as the value of x on each other Ar nucleus, and in another embodiment, one or more value of x differs from other values of x. In one embodiment, in each molecule (VI), each G is the same on each Ar nucleus, and in another embodiment, one or more G differs from other G. In one embodiment, in each molecule (VI), each value of y is the same on each Ar nucleus as the value of y on each other Ar nucleus, and in another embodiment, one or more value of y is different from other values of y. In one embodiment, the An⁻ groups are symmetrically arranged on the Ar nuclei. In one embodiment, the G groups are arranged symmetrically on the Ar nuclei. In one embodiment, the molecule as a whole has at least one axis of symmetry.

In one embodiment, the aromatic polyanionic compound having the general structure (VI) is a compound such as the following aromatic polyanionic compound having the general formula (VI-A) which may be conveniently referred to as AD7, and has the following structure:

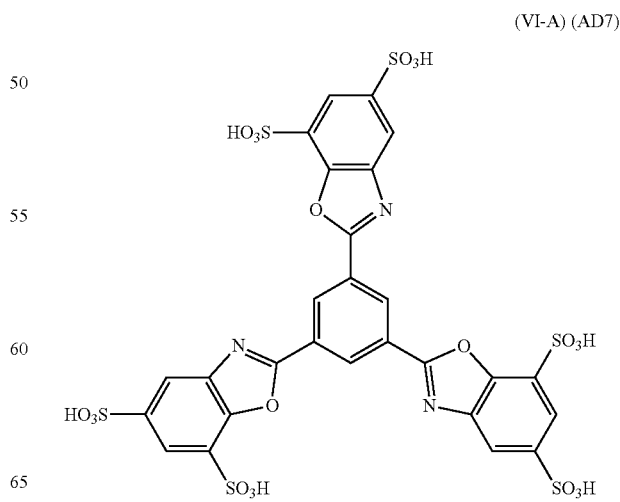

(VI-A) (AD7)

In one embodiment, the polyaromatic polyanionic displacer compound is a cis or trans-stilbene derivative. In this embodiment, the Cen, as defined above, is >C=C< and the ethenyl group is in either a cis or a trans configuration. In this embodiment, the polyaromatic polyanionic displacer compound has a general formula (VII), and when Ar=phenyl, and the compound is trans, the displacer compound has a general formula (VII-A), as shown here:

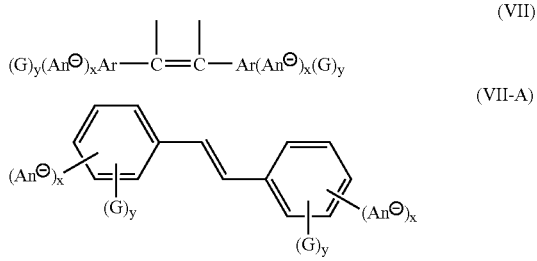

Thus, for example, in this embodiment, the displacer compound may have one of the following exemplary structural formulae (VII-B) or (VII-C):

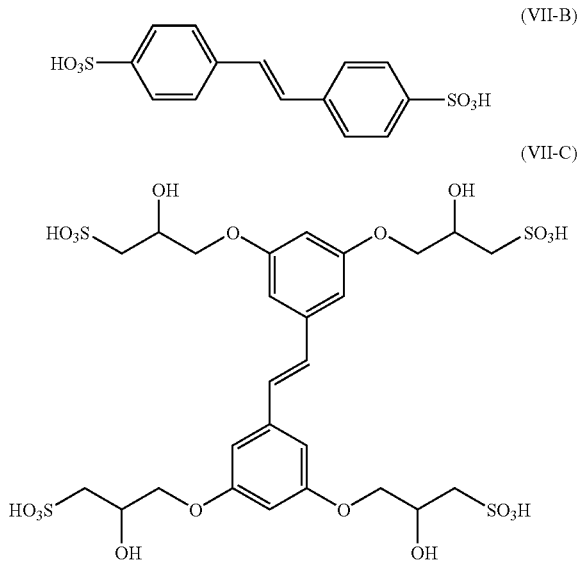

In one embodiment, the polyaromatic polyanionic displacer compound is a compound having the following structural formula (VII-D):

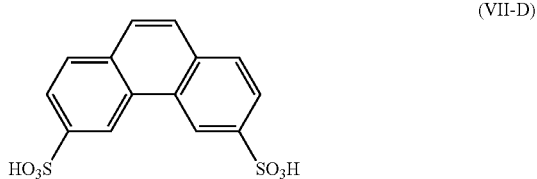 [SMILES: O=S(=O)(O)c1ccc2ccc3ccc(S(=O)(=O)O)cc3c2c1]

The embodiment having structure VII-D is an example of Cen, when as defined above, Cen is >C=C< and the ethenyl group is in a cis configuration, and in which the two phenyl Ar groups are bonded to each other. In this embodiment, y=1 and G constitutes a bond from one Ar group to another Ar group.

In one embodiment, the polyaromatic polyanionic displacer compound of any of the above formulae comprises in the structure an additional substituent that makes it easily detected by UV/Vis spectroscopy, by fluorescence, or any other method known to those skilled in the art. Such a substituent might also influence the affinity of the compound for anion-exchange chromatography, making it either less strongly bound or more strongly bound to the stationary phase. In some cases it would be advantageous to have no substituent that would interfere with the normal means of detecting the compounds being purified by displacement chromatography. An example of this latter case would be a displacer compound of formula I that does not absorb UV light at 280 nm, a wavelength at which certain biopolymers (proteins, oligopeptides, antibodies, etc.) characteristically absorb. Suitable derivatizing agents for enhancing detectability are known to and can be suitably selected by those of skill in the art.

In one embodiment, one or more substituent in the displacer compound in accordance with the present invention may be a group detectable by one or more electromagnetic or radioactive detection methods. Such electromagnetic methods include, for example, UV/visible spectrophotometry and fluorescence spectrophotometry. Suitable radioactive detection methods are known in the art. Suitable substituent groups and appropriate methods for detecting such groups are known to those of skill in the art for use with such methods.

Suitable, exemplary anionic displacer compounds include, for example, the following specific examples which are provided to show examples of displacer compounds. These examples are not intended to be limiting, but are instead intended to provide specific examples illustrating anionic displacer compounds in accordance with various embodiments of the invention.

In accordance with one embodiment of the present invention, the suitable stationary phase is a anion-exchange resin. Suitable anion-exchange resins are known in the art, and generally include resins such as methacrylate, silica, polystyrene or polystyrene-divinylbenzene, which have been derivatized with a cationic moiety, such as secondary, tertiary or quaternary ammonium group, to which anions are attracted. Suitable anion-exchange materials can be selected by those of skill in the art based on the type of materials to be separated. In one embodiment, suitable anion-exchange resins for use with the present invention include, for example, Mono Q, Source 15Q, Q SEPHAROSE® PP and Q SEPHAROSE® FF (Amersham Biosciences); TOYOPEARL® Super Q-5PW, DEAE-650, TSK-GEL Super Q-5PW, and Super Q-650 M (Tosoh Biosep); Unosphere Q, Macroprep High Q (Bio-Rad); PL-SAX (Polymer Labs); SHOWDEX® IEC QA-825 and IEC DEAE-825 (Showa Denko); Q-8HR and DEAE-15HR (Waters); and FRACTOGEL® TMAE and DEAE (EMD Chem.). Other suitable anion-exchange resins known in the art may be used as well.

The resin is generally equilibrated with multiple volumes of anion loading buffer.

Displacement Chromatography Process

In one embodiment, the present invention relates to a displacement chromatography process, comprising:

loading onto a suitable stationary phase a mixture comprising at least one component to be separated;

displacing said at least one component from the stationary phase by applying to the stationary phase a mixture comprising an anionic displacer compound comprising a plurality of anionic groups on one or more aromatic nuclei.

In general, displacement chromatography processes are known to those of skill in the art, as described in the background section above. Accordingly, it is not necessary for the understanding of the present invention by the ordinarily skilled person to describe such process in detail herein, except as in the Examples which follow below.

In accordance with one embodiment of the present invention, the displacement chromatography process can be used to separate and purify DNA, RNA, nucleic acids, nucleotides, oligonucleotides, antisense oligonucleotides, proteins and polypeptides. As used herein DNA is deoxyribonucleic acid obtained from any source, natural or recombinant. As used herein RNA is ribonucleic acid obtained from any source, natural or recombinant, and includes, but is not limited to RNA, mRNA, cRNA, tRNA, nRNA, rRNA and any other known or subsequently prepared or discovered RNA. As used herein, a nucleotide is nucleotide is a monomer or the structural unit of nucleotide chains forming nucleic acids as RNA and DNA. A nucleotide consists of a heterocyclic nucleobase, a pentose sugar (ribose or deoxyribose), and a phosphate or polyphosphate group. A oligonucleotide includes two or more nucleotides, up to about 50 nucleotides, and is considerably smaller than an RNA or DNA molecule. Oligonucleotides are often use a probes for DNA or RNA, and can be used in the PCR (polymerase chain reaction) process. Antisense oligonucleotides are designed and used to hybridize with a particular target RNA to affect the function of the target RNA. The use of an antisense sequence which is complementary by virtue of Watson-Crick base pair hybridization to a specific mRNA, can be used to inhibit expression of the mRNA and thereby result in blocking the transfer of genetic information from DNA into protein. Antisense molecules are designed to interact, for example, with mRNA before it can be translated into the amino acids which make up proteins. In this way, disease-associated proteins can be prevented from forming. These oligonucleotide molecules are called antisense, because they are the Watson-Crick complement to the target RNA.

In one embodiment, the present invention can be used to separate and isolate nucleobases, such as adenine, thymine, uracil, guanine, cytosine, and purines and pyrimidines generally. In one embodiment, the present invention can be used to separate nucleosides, such as adenosine, uridine, guanosine, cytidine, deoxyadenosine, thymidine, deoxyguanosine and deoxycytidine. In one embodiment, the present invention can be used to separate and isolate nucleotides, including, for example, AMP, UMP, GMP, CMP, ADP, UDP, GDP, CDP, ATP, UTP, GTP, CTP, cAMP, and cGMP. In one embodiment, the present invention can be used to separate and isolate deoxynucleotides, including dAMP, dTMP, dUMP, dGMP, dCMP, dADP, dTDP, dUDP, dGDP, dCDP, dATP, dTTP, dUTP, dGTP, and dCTP. In one embodiment, the present invention can be used to separate and isolate nucleic acids, such as DNA, RNA, LNA, PNA, mRNA, ncRNA, miRNA, rRNA, siRNA, tRNA, and mtDNA.

As used herein, a protein is broadly defined as a polyamino acid having a molecular weight greater than about 5 kDa (kilo Daltons), and a polypeptide is a polyamino acid having a molecular weight less than about 5 kDa. As will be understood by those of skill in the art, the difference between a protein and a polypeptide is more one of degree. In general, a protein exhibits tertiary structure, while a polypeptide generally does not.

In one embodiment, the present invention is particularly applicable to separation of components such as proteins and polypeptides from mixtures containing such components. In one embodiment, the one or more component in the mixture comprises one or more polypeptide, one or more protein or a mixture of any two or more such protein and/or polypeptide. That is, the process of the present invention is applicable for separation of mixtures of proteins, mixtures of polypeptides and mixtures of both a protein and a polypeptide In one embodiment, the one or more protein comprises a molecular weight of about 5 kD or higher. In one embodiment, the mixture comprises two or more proteins, two or more polypeptides or a mixture thereof.

In one embodiment, a protein and/or polypeptide from the mixture is displaced from the stationary phase in a fraction in which the protein and/or polypeptide is substantially enriched and/or in which the protein and/or polypeptide is substantially separated from other protein and/or polypeptide components. That is, in one embodiment, when a mixture containing the protein or polypeptide of interest is applied to the stationary phase, when the protein or polypeptide is displaced from the stationary phase and is collected in one or more fraction, the protein and/or polypeptide is obtained in the fraction in either or both of an enriched, i.e., more concentrated, form, or is obtained substantially separated from other, different proteins and/or polypeptide components in the original mixture. Thus, clearly the mixture may include two or more components to be separated. As discussed in the following, in some embodiments, the mixture subjected to displacement chromatography in accordance with the present invention may include a combination of many different materials from a variety of different sources, and the process of the present invention may be usefully applied to such complex mixtures to separate the various components thereof.

In another embodiment, the present invention is applicable to a mixture containing at least one component (such as DNA, RNA, nucleotides, oligonucleotides, protein, polypeptide, drug, drug intermediate, etc.) and at least one impurity. In this embodiment, the process of the present invention may be used to purify the component from one or more impurity with which the desired component may be mixed. Such removal of impurities may be either (1) by immobilization or retention on the stationary phase after the sought or desired component has been displaced (e.g., where the stationary phase acts as a filter), or (2) by being washed out of or eluted from the stationary phase, where the impurity is removed by a means more similar to "traditional" elution chromatography. In this embodiment, when the impurity has been either immobilized on or removed from the column, the desired component can then be removed from the column by displacement chromatography as described herein.

The present invention is applicable to a wide variety of components, including not only the above-mentioned DNA, RNA, nucleotides, oligonucleotides, mixtures thereof and impurities mixed therewith, but many other components.

In one embodiment, the mixture may include one or more, natural or recombinant, antibody or a mixture of any two or more such antibodies. In one embodiment, the mixture may include one or more, natural or recombinant, enzyme or a mixture of any two or more such enzymes. In one embodiment, the mixture may include one or more, natural or recombinant, protein or polypeptide for diagnostic use, or a mixture of any two or more such protein and/or polypeptide. In one embodiment, the mixture may include one or more, natural or recombinant, protein or polypeptide for human or veterinary therapeutic use, or a mixture of any two or more such protein and/or polypeptide. In one embodiment, the mixture may include one or more protein or polypeptide derived from one or more, natural or recombinant, animal or human blood plasma or mixture of any two or more such protein and/or polypeptide. In one embodiment, the mixture may include one or more protein or polypeptide derived from one or more, natural or recombinant, plant material, or mixture of any two or more such protein and/or polypeptide. In one embodiment, the mixture may include one or more protein or polypeptide derived from one or more of animal or human milk or milk derived from a recombinant animal, or mixture of any two or more such protein and/or polypeptide. In one embodiment, the mixture may include one or more protein or polypeptide derived from one or more, natural or recombinant, avian egg, or mixture of any two or more such protein and/or polypeptide. In one embodiment, the mixture may include one or more protein or polypeptide derived from one or more, natural or recombinant, bacterium, yeast, fungus, virus or insect, or mixture of any two or more such protein and/or polypeptide. In one embodiment, the mixture may include one or more protein or polypeptide derived from one or more, natural or recombinant, mammalian cell culture or animal tissue, or mixture of any two or more such protein and/or polypeptide.

In one embodiment, the mixture may include one or more organic compound, drug or drug intermediate, or mixture of any two or more thereof. In one embodiment, one or more of the one or more organic compound, drug or drug intermediate is chiral. In one embodiment, the mixture may comprise a mixture or combination of any of the foregoing, such as a mixture of an antibody and an enzyme, or a mixture of proteins and/or polypeptides obtained from plant material and an avian egg, or any mixture of any of the foregoing exemplary components to which the process of the present invention may be applicable.

In one embodiment, the process of the present invention further includes a step of detecting the anionic displacer compound as it emerges from the stationary phase, wherein the detecting is by one or more of UV/Visible absorption spectroscopy, fluorescence emission spectroscopy, mass spectrometry, pH, conductivity and one or more electrochemical method. The foregoing are the most common applicable methods for detecting the displacer compounds; other suitable methods may be used as known in the art. Such detection may be of one or more detectable substituents as discussed above.

In one embodiment, the method used to detect the component(s) being displaced from the stationary phase can be suitably determined based on the specific component sought. Thus, for example, proteins and polypeptides may be determined based on their UV/visible absorption spectra or wavelengths of characteristic absorption, or by derivatizing them with a visualizing agent. Similarly, drugs and drug intermediates may be determined based on their UV/visible absorption spectra or wavelengths of characteristic absorption.

In one embodiment, the process of the present invention further includes one or more steps of regenerating the stationary phase. In one embodiment, the regenerating may include, for example, treating the stationary phase with a solution of one or more of an alkali metal hydroxide, an alkali metal salt, an alkaline earth hydroxide, an alkaline earth salt, an organic acid, an alkyl sulfonic acid, a quaternary ammonium hydroxide, a quaternary ammonium salt, an alkyl amine, wherein the solution may further comprise a suitable pH buffer. Other suitable regenerating steps may be added, including simple washing with purified water, as needed and as appropriate. In one embodiment, the regeneration includes the use of an organic co-solvent together with water.

In the following examples, exemplary synthetic procedures are provided by which these exemplary anionic displacer compounds may be synthesized. Other suitable anionic displacer compounds within the scope of the invention can be synthesized by methods known to and/or adapted from the foregoing as will be understood by those of skill in the art.

In one embodiment, the displacer composition is free of added dextran sulfate, and in one embodiment the displacer composition is substantially free of dextran sulfate from any source. In one embodiment, the displacer compounds are free of sulfated carbohydrate.

In one embodiment, the displacer compound of the present invention is free of ether groups in the molecule. In one embodiment, the displacer compounds of the present invention comprise polyanionic groups in which adjacent polyanionic groups are not connected by ether-containing moieties. In one embodiment, the displacer compounds of the present invention are free of a dendritic polyether.

In one embodiment, the displacer compounds and compositions of the present invention are substantially free of azo group-containing compounds (azo group is —N=N—). In one embodiment, the displacer compounds and compositions of the present invention are substantially free of anthraquinone-containing compounds. In one embodiment, the displacer composition is substantially free of indigotetrasulfonate.

In one embodiment, the present invention relates to a process for making a polysulfonated polyaromatic compound. In one embodiment, the process includes steps of providing a solution of sulfuric acid; and adding a polyaromatic compound directly to the solution of sulfuric acid. This process has the advantage of directly forming the polysulfonated polyaromatic compound, without forming intermediates that must be isolated and purified.

In one embodiment, the process further includes recovering the polysulfonated polyaromatic compound from the solution. In Example 1 below, an example of a method of recovering the compound is provided.

In one embodiment, the sulfuric acid is concentrated sulfuric acid. In one embodiment, the sulfuric acid is at a temperature of from about 70° C. to about 140° C. when the polyaromatic compound is added thereto.

In one embodiment of this process, the polyaromatic compound is tetraphenylethylene. In this embodiment, in one synthesis, the polysulfonic polyaromatic compound is compound (I-A), which is also referred to herein as AD-1.

While this synthetic process has been described herein with respect to tetraphenylethylene and forms compound (I-A), the process is not limited to use for making this product, but is believed to be useful for making similar polysulfonic polyaromatic compounds.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, in light of the present disclosure, those of skill in the art should appreciate that many changes can be made in the specific embodiments which are disclosed and still obtain a like or similar result without departing from the spirit and scope of the invention, which is limited only by the scope of the appended claims.

Example 1

Synthesis of AD-1

To a 1000 mL 3-neck round bottom flask fitted with a Teflon coated thermocouple is charged 500 mL concentrated sulfuric acid and a magnetic stir bar. The flask is purged with dry nitrogen while a powder addition funnel is charged with 35 g tetraphenylethylene. The powder addition funnel is put in place on the round bottom flask and the flask sealed under an atmosphere of dry nitrogen under slightly superambient pressure. The sulfuric acid is heated with stirring to about 115° C., then the tetraphenylethylene is added to the sulfuric acid in the tetraphenylethylene is added to the sulfuric acid in small portions over about one hour. Each portion of tetraphenylethylene is added only after the previous portion has dissolved in the liquid reaction mixture. When addition is complete, the dark reaction mixture is held at 115° C. for one hour, then allowed to cool to room temperature. The cooled reaction mixture is transferred to an addition funnel and added dropwise over about 4 hours to about 5 liters of ethanol-free ethyl ether cooled to about 5° C. to precipitate the product as an off-while solid. When this addition is complete, stirring is stopped and the solid product is allowed to settle. Approximately 4.5 liters of the supernatant is carefully decanted and the product is slurried in the remaining solvent, then collected on a sintered glass frit under dry nitrogen, washed twice with fresh ether (ethanol-free) and dried under a flow of dry nitrogen. Approximately 64 g of AD1 is recovered as a fine, free-flowing off-white powder that is 99.5% pure by HPLC. If the product retains a trace of sulfuric acid after the ether washes, the product may be dissolved in water and treated with barium carbonate until all sulfuric acid has been removed as barium sulfate. Filtration and evaporation would then yield the pure tetrasulfonic acid suitable for use as a displacer compound on anion-exchange media.

Example 2

Synthesis of AD-2

The synthesis of AD-2 may be carried out in the following two-step procedure.

Step 1: Synthesis of 2-Chloro-4,6-Bis(3-carboxy-4-hydroxy-5-sulfoanilino)-1,3,5-triazine, Disodium Salt (f.w.=621.85)

23 g distilled water and 56 g ice (from distilled water) are placed in a flask and magnetically stirred. The pH and temperature of the ensuing reactions are monitored using a glass pH probe and a temperature probe. 100 mg Triton-X100 detergent is added to the stirring mixture followed by 1.90 g (10.3 mmole, f.w.=184.4) cyanuric trichloride (Aldrich), which is added all at once. For the first part of this reaction, the temperature is maintained in the range 0-5° C. by external cooling if necessary, and the pH is maintained in the range 3.5-4.0 by the addition of small amounts of solid $LiOH.H_2O$ as needed. Portionwise over a period of 2 hours, small amounts of solid 5-amino-3-sulfosalicylic acid (4.80 g, 20.6 mmole, Aldrich) are added to the stirring reaction mixture. The temperature and pH are maintained as stated above. The reaction mixture is then stirred for an additional 4 hours again maintaining the temperature and pH as noted above. The reaction mixture is slowly warmed to room temperature. At this point, the pH is stable at 3.6 and little change is seen. The mixture is stirred overnight (18 hours) at room temperature during which time the pH may drift to 3.5 without the addition of any acid or base. At this point and through out the reaction sequence, the progress of the reaction is followed by anion-exchange HPLC to insure that mono-anilino product is consumed and that the tris-anilino product (melamine) is not formed. Sufficient 2 M HCl is added dropwise to reduce the pH to 1.5, and then the reaction solution is filtered. A saturated NaCl solution (brine) is added dropwise with stirring to the filtrate at room temperature until the product completely crystallizes out of solution (ca 20 mL brine). The reaction mixture is filtered, and the solid product is repeatedly washed with 95% ethanol and then dried under vacuum. This procedure gives 5.58 g (87% yield) of the desired product shown to be about 96% pure by HPLC.

Step 2: 2-(Tris(hydroxymethyl)methylamino)-4,6-Bis(3-carboxy-4-hydroxy-5-sulfoanilino)-1,3,5-triazine, Sodium Salt, (AD2, f.w.=684.55)

15.75 g (130 mmole, f.w.=121.1) Tris(hydroxymethyl)methylamine (Aldrich) and 4.04 g (6.5 mmole, f.w.=621.85) 2-Chloro-4,6-Bis(3-carboxy-4-hydroxy-5-sulfoanilino)-1,3,5-triazine, Disodium Salt (above preparation) are suspended in 40 mL dry, reagent grade dimethylsulfoxide. With stirring, the mixture is heated to 110° C. under a nitrogen atmosphere for 24 hours. The reaction mixture is cooled to room temperature and allowed to stand overnight. Crystals of the starting amine crystallize from solution, and are filtered off. To the filtrate 60 mL distilled water is added, then 6 M HCl is added dropwise until the pH is about 1.5, and finally a saturated NaCl solution (brine) is added dropwise at room temperature until the product crystallizes out of solution (ca 30 mL brine). This reaction mixture is stirred at room temperature for about 1 hour and then filtered. The solid product is repeatedly washed with 95% ethanol and then dried under vacuum to give 3.66 g (82% yield) of the desired product that is about 96% pure by HPLC.

Example 3

Displacement Chromatography of a Protein Mixture

Breakthrough Experiments. Using 5 mM solutions of bovine β-Lactoglobulin A in the loading buffer and of bovine β-Lactoglobulin B in the loading buffer, breakthrough experiments are conducted at various flow rates between 0.1-0.5 mL/min. The loading buffer is prepared from 25 mM BHEP (1,4-Bis (hydroxyethyl)piperazine) and adjusted to pH=7.7 with HCl. Reproducible results are obtained at a flow rate of 0.18 mL/min. The column saturation capacity for bovine β-Lactoglobulin B is 459 mg (108.2 mg/mL), and for bovine β-Lactoglobulin A is 463 mg (109.2 mg/mL). Unpurified lactoglobulins (Sigma) are used straight out of the bottle in these experiments.

Column Preparation. The column (Tosoh Super Q-5PW, 6.0×150 mm) is cleaned and regenerated using Method A (below) and then stored as the chloride form in a sodium chloride buffer, 2.0 M NaCl+25 mM BHEP, pH=7.7 with HCl. The output of the column is passed through a UV/Vis flow-detector monitored at 280 nm and 312 nm, a conductivity flow-cell and a pH flow-cell. The column is equilibrated with loading buffer (see above) at a flow rate of 0.18 mL/min. Once, all three signals (UV absorbance, conductivity, pH) formed stable, level baselines (about 24 min., 1 CV), the displacement experiment is immediately initiated.

Displacement Experiment. Solutions of bovine β-Lactoglobulin B (12.6 mg/mL, Sigma#L8005) and bovine β-Lactoglobulin A (13.4 mg/mL, Sigma#L7880) are prepared in the loading buffer (see above). The protein concentrations are determined using BCA-Copper and Bradford assays. Equal volumes of the two cytochrome solutions are mixed, loaded into a 20.0 mL sample loop and then pumped onto a cleaned and properly equilibrated anion-exchange column (see above) at a constant flow rate of 0.36 mL/min. for 57 minutes. The loop is switched out of the input flow path, and the loading buffer is pumped through the column for 12 minutes at 0.36 mL/min. Finally, a 5.0 mM AD1 displacer solution in the loading buffer is pumped onto the column at 0.18 mL/min., and the output of the column is passed through a UV/Vis flow-detector (10 µL flow-cell, monitored at 280, 312, 380 nm) into a fraction collector. Fractions are collected every 1.00 min.; owing to prior experience, the initial fractions without protein are discarded. Conductivity and pH flow-cells (see above) are usually in the output path behind the UV/Vis detector in order to monitor the course of the displacement experiment; however, when fractions are collected, these two cells are switched out of the flow path so as not to broaden the transition between displacement peaks. Once collected, the fractions are sealed and refrigerated for subsequent HPLC analysis. The displacement experiment is carried out at ambient temperature, 22° C. The displacement trace is shown in FIG. 1.

HPLC Analysis of Lactoglobulins. The details of the HPLC fraction analysis are given below.

Column:
 Stainless Steel column 4.6×200 mm internal dimensions
 Manufactured by PolyLC (Columbia, Md.)
 PolyWAX LP, weak anion-exchange silica-based matrix
 5µ particle size, 300 angstrom pore size
Buffer Solvent: HPLC grade distilled water
Elution Buffers:
 A—50 mM N(CH$_2$CH$_2$OH)$_3$, pH=7.8 with HCl, solvent 10/90 (v/v) acetonitrile/water
 B—0.50 M NaCl+50 mM N(CH$_2$CH$_2$OH)$_3$, pH=7.8 with HCl, solvent 10/90 (v/v) acetonitrile/water
 Elution buffers are filtered through 0.2µ filter to remove particulates.
Flow Rate: Constant flow rate is 1.0 mL/min.

| Gradient Method | |
| --- | --- |
| 0-2 min | 100% A, isocratic |
| 2-52 min | 100% A to 100% B, linear gradient |
| 52-56 min | 100% B, isocratic |

UV Detector Wavelengths 312 nm and 380 nm–AD1 only 280 nm–proteins+AD1

Sample Prep: 10 µL of the fraction sample and 140 µL of dilution buffer are mixed and 50 µL of this mixture is injected onto the column. Exact dilution factors are determined by weight.

Figure 2:
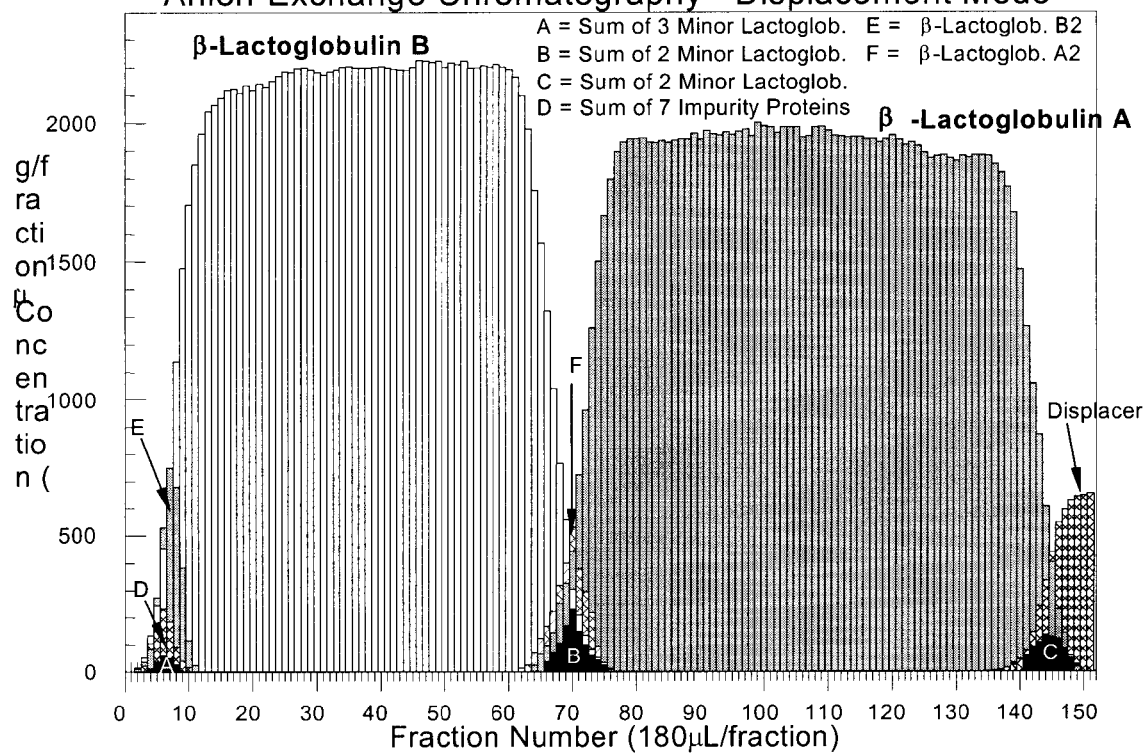
FIG. 2 is a graph depicting the concentration of fractions collected during displacement chromatography of a mixture of bovine β-lactoglobulin A and bovine β-lactoglobulin B, in accordance with an embodiment of the invention.

Under this analysis, each Sigma lactoglobulin showed one major peak, one major isoform peak, several (3-4) small isoform peaks and several (4-5) small peaks due to impurity proteins. Out of the bottle, bovine β-Lactoglobulin B is about 95% pure (based on protein impurities) and bovine β-Lactoglobulin A is about 97% pure. Unlike β-Lactoglobulin A, β-Lactoglobulin B contained significant levels of inorganic salts and buffers. All 151 collected samples are thus analyzed, and data from 280 nm are displayed in FIG. 2 and the table below. The recovery of total protein from the column is 97%.

| Purified protein: | Lacto B | Lacto A |
| --- | --- | --- |
| Sample pool: | 12-61 | 77-137 |
| HPLC purity: | >99.9% | >99.9% |
| Recovery: | 103.2 mg | 112.0 mg |
| % Recovery:[1] | 84.6% | 86.2% |
| % Recovery:[2] | 81.9% | 83.6% |
| Measured AD1:* | ND (<0.5 ppm) | 1.3 ppm |
| Estimated AD1:* | <50 ppb | 1.1 ppm |

ND = not detected
*before concentration or dialysis in pooled fractions.
[1] of main peak.
[2] of total protein.

Column Cleaning and Regeneration Protocols. Owing to the strong binding of AD1 to most anion-exchange matrices, we found sodium bromide to be more useful that sodium chloride for most matrices. Occasionally sodium succinate or sodium citrate are used.

Method A: Cleaning+Regeneration (regeneration efficiency 99%) (All flows are at 0.64 mL/min.)

| | | |
| --- | --- | --- |
| 2.0M NaBr + 0.1M Glycine, pH = 2.5 w/HBr, 80/20 (v/v) water/acetonitrile | 133 min | 20 CV |
| 0.1M Triethanolamine, pH = 7.8 w/HBr | 17 min | 2.5 CV |
| 0.1M NaOH | 30 min | 4.5 CV |
| 0.1M Triethanolamine, pH = 7.8 w/HBr | 17 min | 2.5 CV |
| 2.0M NaCl + 25 mM BHEP, pH = 7.7 | 34 min | 5 CV |

Method B: Cleaning+Regeneration (regeneration efficiency 100%) (All flows are at 0.64 mL/min.)

| | | |
| --- | --- | --- |
| 2.0M (CH$_3$)$_4$NBr + 0.1M Glycine, pH = 2.5 w/HBr, 80/20 (v/v) water/acetonitrile | 100 min | 15 CV |
| 0.1M Triethanolamine, pH = 7.8 w/HBr | 17 min | 2.5 CV |
| 0.1M (CH$_3$)$_4$NOH | 30 min | 4.5 CV |
| 0.1M Triethanolamine, pH = 7.8 w/HBr | 17 min | 2.5 CV |
| 2.0M NaCl + 25 mM BHEP, pH = 7.7 | 34 min | 5 CV |

Example 4

Syntheses of Polyanionic Biphenyl Compounds

The displacer compounds disclosed herein include the polyanionic biphenyl compounds having the general structure (IV-C) shown above. Specific examples of such polyanionic biphenyl compounds are shown in FIG. 3.

Figure 3:
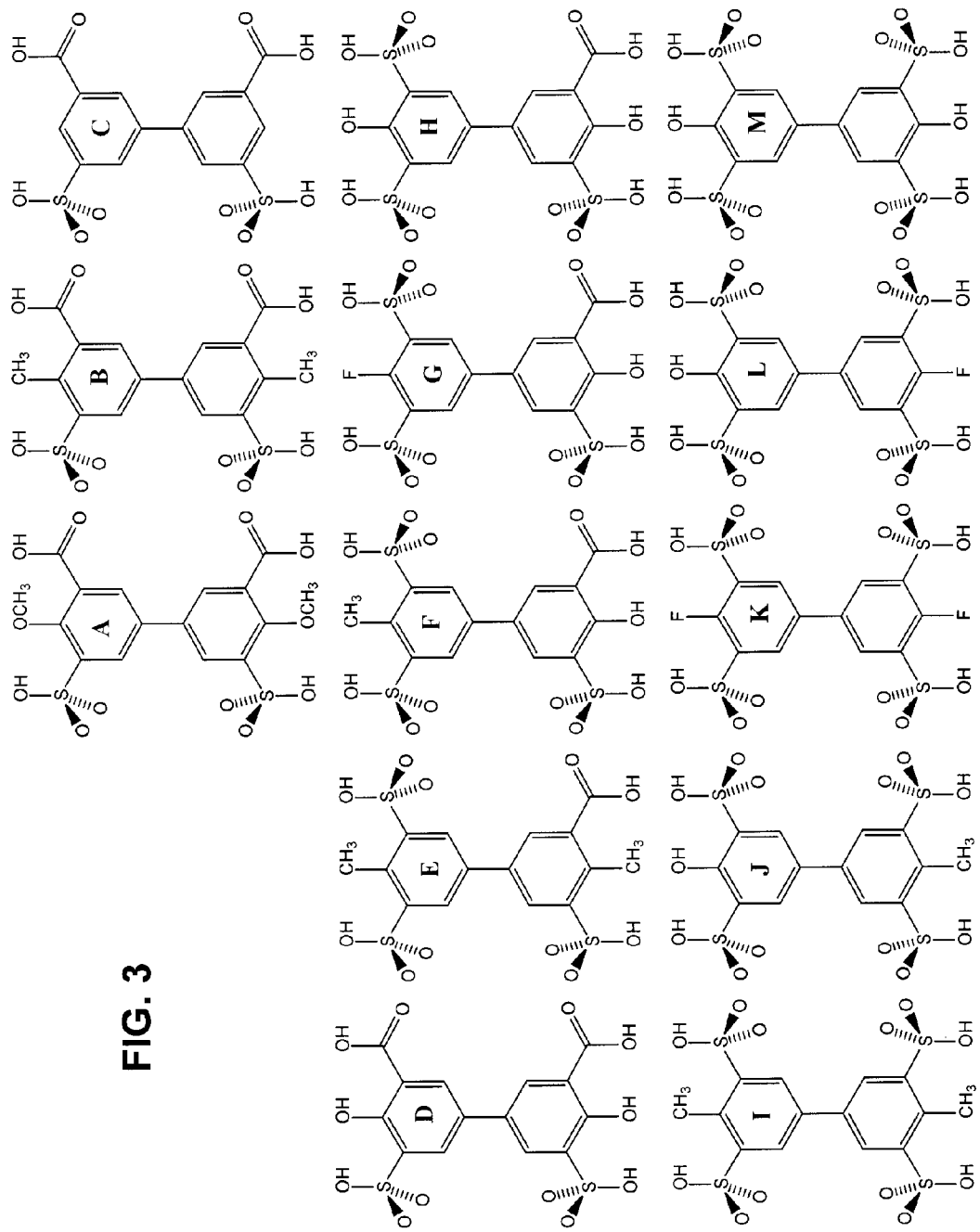
FIG. 3 depicts the structural formulae of a plurality of compounds in accordance with embodiments of the present invention.

The following disclosure provides details of the syntheses of at least some of the polyanionic biphenyl compounds exemplified in FIG. 3. It will be recognized by those of skill in the art that the many other isomers and congeners of these exemplary polyanionic biphenyl compounds can be synthesized by similar methods adapted as needed. All of the polyanionic biphenyl compounds having the general structure (IV-C) have utility as displacer compounds, as described herein.

As shown in FIG. 3, the exemplary compounds are designated by the letters A-M, where the letter is shown over one of the aromatic rings. In the following, the compounds are referred to by these letters A-M as appropriate. As noted above, compound I in FIG. 3 corresponds to structure (IV-B) shown above.

The starting biphenyl compounds are shown below, first by their chemical names and then by the designations a-m for ease of reference, corresponding to the resulting polyanionic biphenyl compounds A-M.

The starting biphenyl compounds a-m may be synthesized by known methods from the starting materials shown in the following Table 1.

Each of the polyanionic biphenyl compounds may be prepared by the methods described below and summarized in the following Table 2.

and then concentrated aqueous HCl solution (37%) is carefully added dropwise until the pH of the mixture was less than 1.0. Upon acid addition, a white product begins to crystallize

TABLE 1

Syntheses of Starting Biphenyls

| Biphenyl Name | Method | Starting Material | Purity |
|---|---|---|---|
| 4,4'-Dimethoxybiphenyl-3,3'-dicarboxylic Acid (a) | 1 | 5-Bromo-o-anisic Acid | >99% |
| 4,4'-Dimethylbiphenyl-3,3'-dicarboxylic Acid (b) | 1 | 5-Bromo-o-toluic Acid | >99% |
| Biphenyl-3,3'-dicarboxylic Acid (c) | 1 | 3-Bromobenzoic Acid | >99% |
| 4,4'-Dihydroxybiphenyl-3,3'-dicarboxylic Acid (d) | 1 | 5-Iodosalicyclic Acid | >99% |
| 4,4'-Dimethylbiphenyl-3-carboxylic Acid (e) | 3 | 5-Bromo-o-toluic Acid + p-Tolylboronic Acid | >99% |
| 4-Hydroxy-4'-methylbiphenyl-3-carboxylic Acid (f) | 3 | 5-Iodosalicyclic Acid + p-Tolylboronic Acid | >99% |
| 4-Hydroxy-4'-fluorobiphenyl-3-carboxylic Acid (g) | 3 | 5-Iodosalicyclic Acid + 4-Fluorophenylboronic Acid | >99% |
| 4,4'-Dihydroxybiphenyl-3-carboxylic Acid (h) | 3 | 5-Iodosalicyclic Acid + 4-Hydroxyphenylboronic Acid | >99% |
| 4,4'-Dimethylbiphenyl (i) | 2 | 4-Bromotoluene | >99% |
| 4-Hydroxy-4'-methylbiphenyl (j) | 4 | 4-Bromophenol + p-Tolylboronic Acid | >99% |
| 4,4'-Difluorobiphenyl (k) | 2 | 4-Bromofluorobenzene | >99% |
| 4-Fluoro-4'-hydroxybiphenyl (l) | 4 | 4-Bromophenol + 4-Fluorophenylboronic Acid | >99% |
| 4,4'-Dihydroxybiphenyl (m) | 2 | 4-Bromophenol | >99% |

TABLE 2

Syntheses of Polyaromatic Biphenyl Compounds

| Displacer Name | Method | S/M[a] | Yield | Purity | Retention |
|---|---|---|---|---|---|
| 3,3'-Dicarboxy-4,4'-dimethoxybiphenyl-5,5'-disulfonic Acid (A) | 5a: 24 hr @ 40 C. | a | 65% | 89% | [b]24.6 |
| 3,3'-Dicarboxy-4,4'-dimethylbiphenyl-5,5'-disulfonic Acid (B) | 5a: 24 hr @ 70 C. | b | 92% | >98% | 24.7 |
| 3,3'-Dicarboxybiphenyl-5,5'-disulfonic Acid (C) | 5a: 24 hr @ 70 C. | c | 52% | 77% | [c]27.7 |
| 3,3' Dicarboxy-4,4'-dihydroxybiphenyl-5,5'-disulfonic Acid (D) | 5a: 24 hr @ 70 C. | d | 96% | >98% | 32.6 |
| 3-Carboxy-4,4'-dimethylbiphenyl-3',5,5'-trisulfonic Acid (E) | 5b: 12 hr @ 30 C.; 24 hr @ 70 C. | e | 87% | >98% | 28.6 |
| 3-Carboxy-4-hydroxy-4'-methylbiphenyl-3',5,5'-trisulfonic Acid (F) | 5b: 24 hr @ 30 C.; 24 hr @ 70 C. | f | 84% | >98% | 33.0 |
| 3-Carboxy-4-hydroxy-4'-fluorobiphenyl-3',5,5'-trisulfonic Acid (G)[d] | 5b: 24 hr @ 30 C.; 120 hr @ 110 C. | g | 66% | 94% | 34.0 |
| 3-Carboxy-4,4'-dihydroxybiphenyl-3',5,5'-trisulfonic Acid (H) | 5b: 3 hr @ 30 C.; 3 hr @ 70 | h | 81% | >98% | 34.7 |
| 4,4'-Dimethylbiphenyl-3,3',5,5'-tetrasulfonic Acid (I)[e] | 5c: 6 hr @ 30 C.; 6 hr @ 70 C. | i | 90% | >98% | 34.1 |
| 4-Hydroxy-4'-methylbiphenyl-3,3',5,5'-tetrasulfonic Acid (J)[e,f] | 5c: 3 hr @ 30 C.; 3 hr @ 70 C. | j | 75% | 97% | 35.3 |
| 4,4'-Difluorobiphenyl-3,3',5,5'-tetrasulfonic Acid (K) | 5c: 24 hr @ 30 C.; 72 hr @ 110 C. | k | 65% | >98% | 35.4 |
| 4-Fluoro-4'-hydroxybiphenyl-3,3',5,5'-tetrasulfonic Acid (L)[e,f] | 5c: 24 hr @ 30 C.; 72 hr @ 110 C. | l | 64% | 96% | 36.1 |
| 4,4'-Dihydroxybiphenyl-3,3',5,5'-tetrasulfonic Acid (M)[e,f] | 5c: 3 hr @ 30 C.; 2 hr @ 70 C. | m | 73% | >98% | 36.8 |
| Tetrakis(4-sulfophenyl)ethylene | — | — | — | — | 28.0 |

[a]Starting Material.
[b]Major impurity: 3,3'-Dicarboxy-4-hydroxy-4'-methoxybiphenyl-5,5'-disulfonic Acid (retention = 30.6)
[c]Major impurity: 3,3'-Dicarboxybiphenyl-4,5'-disulfonic Acid (retention = 25.1)
[d]Poorly soluble intermediate crystallized out and then slowly redissolved.
[e]Compound to be sulfonated was added portionwise with cooling to prevent initial exotherm.
[f]Propionitrile or acetonitrile not added during crystallization.

The methods referred to above in Tables 1 and 2, e.g., the methods 1-4 for preparing the biphenyl compounds, and methods 5a-5c for preparing the polyanionic biphenyl compounds, are described in the following. As will be recognized by those of skill in the art, the following syntheses may be modified as needed to obtain the desired product.

Method 1: 4,4'-Dimethylbiphenyl-3,3'-dicarboxylic Acid (b) (fw=270.28)

28.02 g NaOH solution (50% aqueous, 350 mmole, fw=40.01), 90.0 g distilled water and 0.42 g 5% Pd/C catalyst are placed in a 250 mL three-necked, round-bottom flask and then warmed to 40° C. for 5 minutes with magnetic stirring. 2.11 g formylhydrazine (35 mmole, fw=60.06) is added, and the mixture is stirred at 40° C. for an additional 10 minutes. Then 21.51 g 5-bromo-o-toluic acid (100 mmole, fw=215.05) is added portionwise over a period of 15 minutes resulting in vigorous $N_2$ evolution and a mild exotherm (ca 60° C.). The reaction mixture is heated to 85° C. and maintained at this temperature for 3 hours.

In order to remove the catalyst, the warm reaction mixture is passed through a paper filter. The filtrate is heated to 90° C., from the hot solution. The hot mixture (ca 70-80° C.) is rapidly filtered through a glass filter, washed with dilute aqueous HCl (ambient temperature) and then distilled water (ambient temperature). The product is allowed to dry by sucking air through the filter. Isolated yield is about 11.62 grams (86%) of a white crystalline powder.

Method 2: 4,4'-Difluorobiphenyl (m) (fw=190.19)

60.02 g NaOH solution (50% aqueous, 750 mmole, fw=40.01), 77.08 g $(CH_3)_4OH$ solution (37% aqueous, 313 mmole, fw=91.12) and 1.60 g 5% Pd/C catalyst are placed in a 500 mL three-necked, round-bottom flask and then warmed to 40° C. for 5 minutes with vigorous magnetic or mechanical stirring. 15.80 g formylhydrazine (263 mmole, fw=60.06) is added, and the mixture is stirred at 40° C. for an additional 10 minutes. Then a mixture of 75.0 g 1,2-dimethoxyethane (DME) and 131.3 g 4-bromofluorobenzene (750 mmole, fw=174.96) is added over a period of 15 minutes using an addition funnel. Vigorous $N_2$ evolution is observed along with a mild exotherm (ca 65° C.). The reaction mixture is heated to 75° C. and maintained at this temperature for 3 hours. For similar compounds, the reaction mixture is usually heated to 85° C., but here 75° C. is used in order to reduce losses of the product via unwanted sublimation. The lower boiling tetrahydrofuran is sometimes used instead of DME.

The residual base is neutralized using concentrated HCl, and then the catalyst is removed by passing the warm reaction mixture through a paper filter which is subsequently washed with diethyl ether. The upper organic layer is separated from the lower aqueous layer using a separatory funnel. The aqueous layer is extracted once using 250 mL diethyl ether; the upper organic layer is separated and combined with the first organic layer. The combined organic layer is dried over anhydrous magnesium sulfate and filtered away from the solids which are also washed with ether. The organic layer is placed on a rotary evaporator at reduced pressure; the ether is first removed followed by the DME. A colorless oil forms which turns into beautiful white crystals. Most, but not all of the DME is removed under reduced pressure because too much of the product is otherwise lost via sublimation. The residual liquid is carefully drained off from the white crystals which are subsequently washed with cold (−20° C.) n-pentane. The drained liquid is combined with an equal volume of n-pentane and cooled to −20° C. overnight from which a second crop of pure crystals is obtained. The product is allowed to dry by briefly sucking air through it on the glass filter; this process is not carried out too long in order to avoid excessive product loss. Isolated yield is about 54.92 g (77%) of a white crystalline powder. The final product is sufficiently enough purity (>99%) for most applications. If needed, the product can be sublimed or recrystallized from warm n-hexane.

Method 3: 4,4'-Dimethylbiphenyl-3-carboxylic Acid (e) (fw=226.27)

28.54 g tetramethylammonium carbonate solution (27% aqueous, 37 mmole, fw=208.30), 24.0 g distilled water and 30.0 g PEG-2000 are placed in a 100 mL three-necked, round-bottom flask and then heated to 50° C. with magnetic stirring. The system is degassed and placed under an $N_2$ atmosphere. 23 mg palladium acetate (0.10 mmole, fw=224.50) is added to the stirring mixture. After several minutes, the palladium compound is fully dissolved, and the system is again degassed and the temperature is reduced to 30° C. 2.15 g (10 mmole, fw=215.05, finely powdered) 5-bromo-o-toluic acid is added all at once to the stirring mixture, and then the system is degassed. Dissolution is accomplished within several minutes. Finally, 1.64 g (12 mmole, fw=135.96, finely powdered) 4-tolylboronic acid is added to the stirring mixture which is again degassed. The reaction mixture is maintained at 30° C. for 1 hour and then raised to 50° C. until the bromotoluic acid is fully reacted (>99.5% conversion, measured by AIX HPLC). Total heating time after addition of reactants is about 1.5 hours.

In order to remove the precipitated palladium, the warm reaction mixture is filtered through a bed of Celite over #5 Whatman paper filter, and then the Celite is washed with 85 mL 2.5% tetramethylammonium carbonate solution at ambient temperature. The combined reaction mixture and wash are heated to 90° C. and then concentrated aqueous HCl solution (37%) is carefully added dropwise until the pH of the mixture is less than 1.0. Upon acid addition, considerable amounts of $CO_2$ are released and then the white product begins to crystallize from the hot solution. The hot mixture (ca 80° C.) is rapidly filtered through a glass filter, washed with dilute aqueous HCl (ambient temperature) and then 50/50 acetonitrile-water (ambient temperature), and finally allowed to dry by sucking air through the filter. Isolated yield is 2.07 grams (91%) of a white, crystalline powder.

Method 4: 4-Methyl-4'-hydroxybiphenyl (i) (fw=184.24)

2.34 g anhydrous sodium carbonate (22 mmole, fw=105.99), 1.73 g 4-bromophenol (10 mmole, fw=173.01), 35 mL distilled water and 35 mL acetone are placed in a 100 mL three-necked, round-bottom flask and then heated to 35° C. with magnetic stirring. 11 mg palladium acetate (0.049 mmole, fw=224.50) is added to the stirring mixture. After several minutes, the palladium compound is fully dissolved, and 1.77 g (13 mmole, fw=135.96) p-tolylboronic acid is added all at once to the stirring mixture. The system is degassed and placed under an $N_2$ atmosphere. The reaction mixture is maintained at 35° C. for 1 hour.

Concentrated aqueous HCl is added dropwise to neutralize the residual base (carbonate), and then the acetone is removed under reduced pressure. The product along with the some residual catalyst is removed by filtration. The solid is dissolved in 50 mL diethyl ether and dried over anhydrous magnesium sulfate. The solids are removed by filtration, and the ether is removed under reduced pressure yielding 1.61 g crude product. The crude product is recrystallized from hot ethanol-water (50/50 w/w) or hot n-hexane to give 1.22 g (66%) of white crystals.

Method 5a: 3,3'-Dicarboxy-4,4'-dihydroxybiphenyl-5,5'-disulfonic Acid (D) (fw=434.35)

Purified 4,4'-dihydroxybiphenyl-3,3'-dicarboxylic acid is dried in an oven at 110° C. for several hours to remove residual water, and then 13.72 g (50 mmole, fw=274.23) is added all at once to single-neck 100 mL flask containing 53.4 g 30% fuming $H_2SO_4$ (fresh bottle of known concentration, 200 mmole $SO_3$, $fw_{(SO3)}$=80.06). The flask is fitted with an efficient condenser to return $SO_3$ to the reaction mixture and a good Teflon-coated magnetic stirrer. The reaction is carried out under a dry $N_2$ atmosphere with a slight positive pressure in order to keep out moist air. The viscous mixture is stirred at ambient temperature for about 30 minutes to insure that the solid is evenly dispersed in the sulfuric acid solvent. The flask is partly immersed in an oil bath maintained at 70° C., and then stirred for the requisite amount of time, usually about 24 hours. Within several minutes to several hours, the reaction becomes clear, and stirring becomes more efficient in the homogeneous medium with lower viscosity. The reaction mixture can be monitored using AIX HPLC to observe the appearance and then complete disappearance of the monosulfonated intermediate. After the oil bath is removed, the reaction mixture is allowed to cool to ambient temperature, and then 14.8 g distilled water is carefully added dropwise to the stirring mixture. The water addition is very exothermic and is controlled by the rate of water addition or sometimes external cooling. The temperature of the reaction mixture is maintained between 70-85° C. until water addition is complete. The reaction product is appreciably soluble in pure sulfuric acid, but much less so in 75% sulfuric acid. The reaction mixture is allowed to cool to room temperature with stirring. After several hours (sometimes overnight), the white product crystallizes from solution often forming a solid mass. If the cooling mixture is seeded with crystals of the product, crystallization takes place much faster. All 4,4'-dihydroxybiphenyls are protected from air at elevated temperatures to prevent unwanted oxidation. The reaction mixture is cooled to 4° C. for several hours and then added to 110 mL cold propionitrile with stirring; sometimes actonitrile is substituted for the propionitrile. This mixture further promotes crystallization and facilitates removal of the acid by filtration. After standing for several hours at 4° C., the mixture is filtered using a glass filter and dried by passing dry air or $N_2$ through the filter overnight to give 22.5 g (96%) of the pure disulfonated product as white crystals of the dihydrate.

Method 5b: 3-Carboxy-4-hydroxy-4'-methylbiphenyl-3',5,5'-trisulfonic Acid (F) (fw=468.43)

The same procedure as 5a is used with 11.42 g dry 4-hydroxy-4'-methylbiphenyl-3-carboxylic acid (50 mmole, fw=228.25) and 80.1 g 30% fuming sulfuric acid (300 mmole, fw=80.06) which are stirred at 30° C. for 24 hour and then heated with stirring at 70° C. for another 24 hours. Crystallization was effected using 22.2 g distilled water and 145 mL propionitrile. Yield was 21.2 g (84%) of the trisulfonated product as white crystals of the dihydrate.

Method 5c: 4,4'-Difluorobiphenyl-3,3',5,5'-tetrasulfonic Acid (K) (fw=510.44)

The same procedure as 5a is used with 9.51 g dry 4,4'-difluorobiphenyl (50 mmole, fw=190.19) and 106.8 g 30% fuming sulfuric acid (400 mmole, fw=80.06) which are stirred at 30° C. for 24 hour and then heated with stirring at 110° C. for another 72 hours. Crystallization was effected using 29.6 g distilled water and 185 mL propionitrile. Yield was 17.2 g (65%) of the tetrasulfonated product as white crystals of the monohydrate.

As will be understood by those of skill in the art, similar and analogous methods may be used to prepare the compounds shown in FIG. 3, all of which are described by the general formula (IV-C), shown above.

All of the compositions and processes disclosed and claimed herein can be made and executed by those of ordinary skill in the art without undue experimentation in light of the present disclosure and based upon the knowledge of such persons. While the compositions and processes of this invention have been described in terms of certain preferred embodiments, it will be apparent to those of ordinary skill in the art that variations may be applied to the compositions and/or processes and in the steps or in the sequence of steps of the processes described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A displacement chromatography process, comprising:
   loading onto a stationary phase comprising an anion-exchange material a mixture comprising one or more component to be separated;
   displacing at least one of the one or more component from the stationary phase by applying to the stationary phase a mixture comprising a polyaromatic polyanionic displacer compound having the general formula:

$Cen(Ar)_w$ wherein Cen=a bond, an alkenyl group, an alkynyl group, a benzene ring, a biphenylene, a naphthylene, or

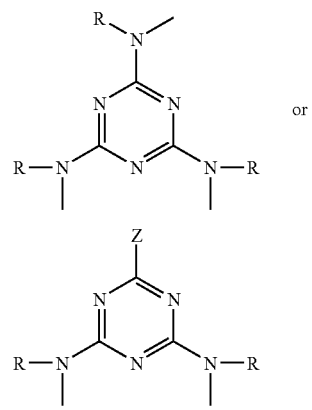

wherein:
R=independently —H, $C_1$-$C_4$ alkyl, or $C_1$-$C_4$ hydroxyalkyl;
Z=independently —H, halogen, —OH, —OR, —NRCH$_2$CH(OH)CH$_2$OH, —NR$_2$, —N[CH$_2$CH(OH)CH$_2$OH]$_2$, —NRC(CH$_2$OH)$_3$, —NRCH(CH$_2$OH)$_2$, or —N(R)(poly(alkylene oxide));
w=2 to the highest number of substitutable positions on Cen; and
Ar=(a), (b) and/or (c); and wherein, in the following (a), (b) and (c):
An$^-$=independently sulfonate, phosphonate, phosphinate, phosphate, a phosphate mono- or di-ester, sulfate, a sulfate mono-ester; or boronate;
G=independently H, $C_1$-$C_6$ alkyl, $C_1$-$C_6$ alkenyl, $C_6$-$C_{10}$ aryl, halogen, nitro, hydroxy, $C_1$-$C_6$ alkoxy, cyano, —NH$_2$, —NRH, —NR$_2$, —NHC(O)R, —CHO, —C(O)R; and
(a), (b) and (c) are:

(a)

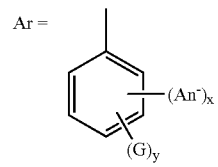

wherein in (a):
x = 1 - 3, provided that in at least one Ar, x = 2 or 3, and further provided that when Cen is a direct bond,
x = 2 or 3 in at least two Ar
y = 2 - 4
x + y = 5; and/or (b)

Ar =

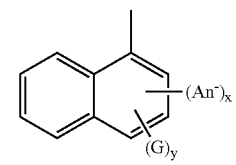

or

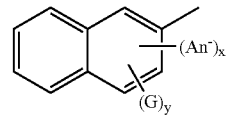

wherein in either (b):
x = 1 - 3
y = 4 - 6
x + y = 7; and/or

-continued

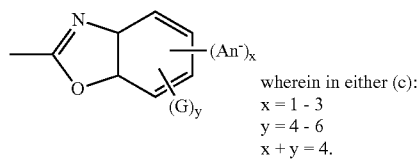

wherein in either (c):
x = 1 - 3
y = 4 - 6
x + y = 4.

2. The process of claim 1 wherein the one or more component comprises one or more polypeptide, one or more protein, one or more natural or recombinant oligonucleotide, one or more natural or recombinant DNA, one or more natural or recombinant RNA, or a mixture of any two or more thereof.

3. The process of claim 1 wherein the component of the mixture is displaced from the stationary phase in a fraction in which the component is substantially enriched and/or in which the component is substantially separated from other components of the mixture.

4. The process of claim 1 wherein the mixture comprises at least two components to be separated.

5. The process of claim 1 wherein the mixture comprises the at least one component and at least one impurity.

6. The process of claim 1 further comprising detecting one or more of the component and the displacer compound as it emerges from the stationary phase, wherein the detecting is by one or more of UV/Visible absorption spectroscopy, fluorescence emission spectroscopy, mass spectrometry, pH, conductivity and one or more electrochemical method.

7. The process of claim 1 further comprising regenerating the stationary phase.

8. The process of claim 7 wherein the regenerating comprises treating the stationary phase with a solution of one or more of an alkali metal hydroxide, an alkali metal salt, an alkaline earth hydroxide, an alkaline earth salt, an organic acid, an alkyl sulfonic acid, a quaternary ammonium hydroxide, a quaternary ammonium salt, an alkyl amine, wherein the solution may further comprise a suitable pH buffer.

9. The process of claim 7 wherein the regenerating comprises treating the stationary phase with a solution comprising water and an organic co-solvent.

10. The process of claim 1 wherein the polyaromatic polyanionic displacer compound has formula (I):

(I)

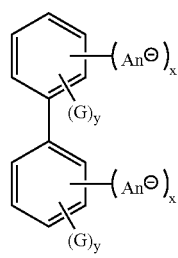

wherein in (I), each An⁻, each G, each x and each y may be selected independently and are defined as in claim 1.

11. The process of claim 1 wherein the polyaromatic polyanionic displacer compound has formula (II):

(II)

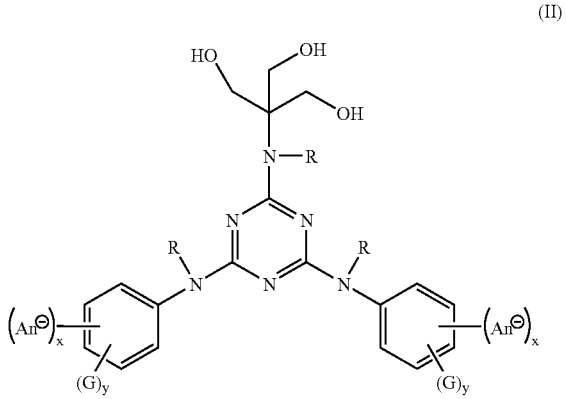

wherein in (II), each An⁻, each G, each R, each x and each y may be selected independently and are defined as in claim 1.

12. The process of claim 1 wherein the polyaromatic polyanionic displacer compound has formula (III):

(III)

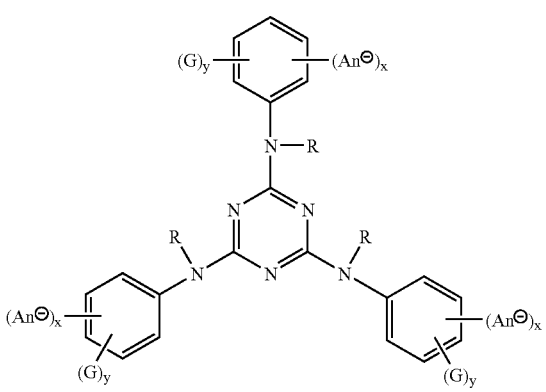

wherein in (III), each An⁻, each G, each R, each x and each y may be selected independently and are defined as in claim 1.

13. The process of claim 1 wherein the polyaromatic polyanionic displacer compound has formula (IV):

(IV)

wherein in (IV), each An⁻, each G, each x and each y may be selected independently and are defined as in claim 1.

14. The process of claim 13 wherein the displacer compound has formula (IV-A):

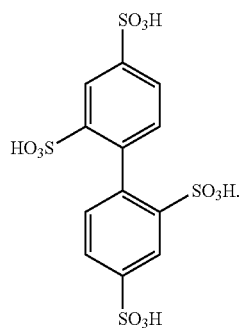
(IV-A)

15. The process of claim 13 wherein the displacer compound has formula (IV-B):

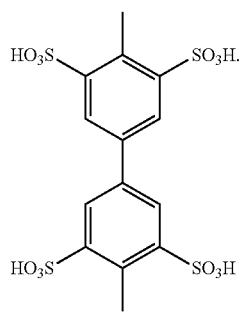
(IV-B)

16. The process of claim 13 wherein the polyaromatic polyanionic displacer compound has formula (IV-C):

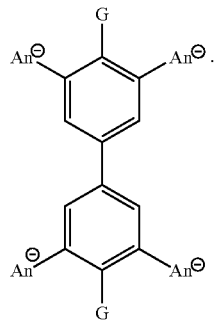
(IV-C)

17. The process of claim 1 wherein the polyaromatic polyanionic displacer compound has formula (V):

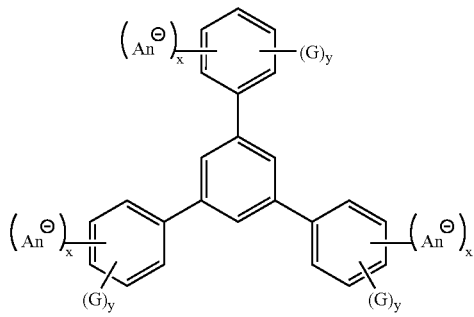
(V)

wherein in (V), each $An^-$, each G, each x and each y may be selected independently and are defined as in claim 1.

18. The process of claim 1 wherein the polyaromatic polyanionic displacer compound has formula (VI):

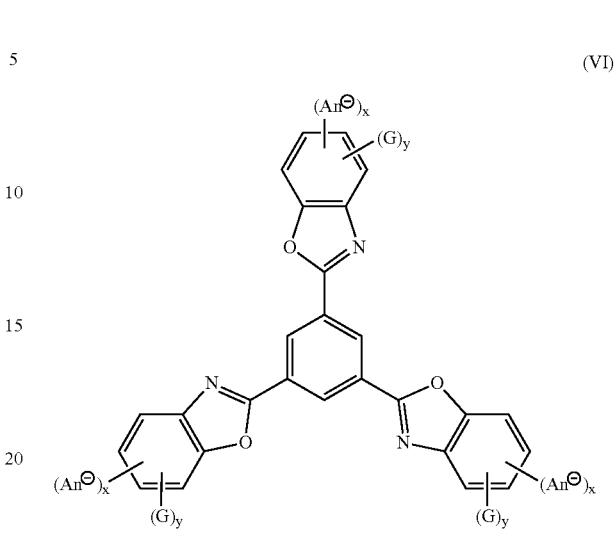
(VI)

wherein in (VI), each $An^-$, each G, each x and each y may be selected independently and are defined as in claim 1.

19. The process of claim 18 wherein the displacer compound has the formula (VI-A):

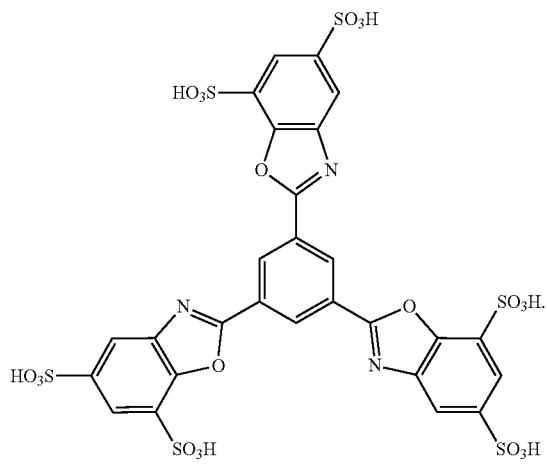
(VI-A)

20. The process of claim 1 wherein the displacer compound has the formula (VII) or (VII-A):

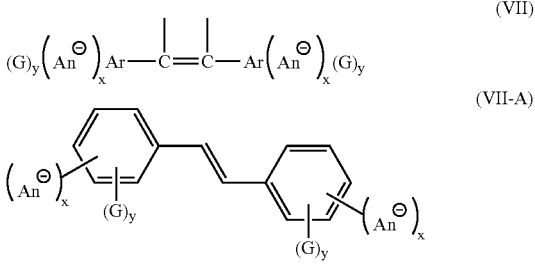
(VII)
(VII-A)

wherein in (VII) and (VII-A), each An⁻, each G, each x and each y may be selected independently and are defined as in claim 1.

21. The process of claim 20, wherein the displacer compound has the formula (VII-C):

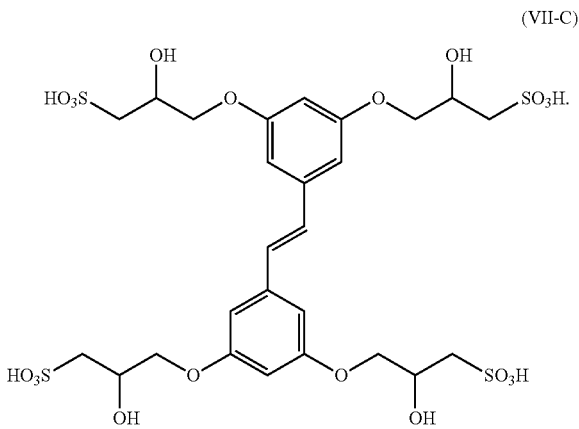 [SMILES: O=S(=O)(O)CC(O)COc1cc(/C=C/c2cc(OCC(O)CS(=O)(=O)O)cc(OCC(O)CS(=O)(=O)O)c2)cc(OCC(O)CS(=O)(=O)O)c1]

(VII-C)

22. The process of claim 20, wherein the displacer compound has the formula (VII-D):

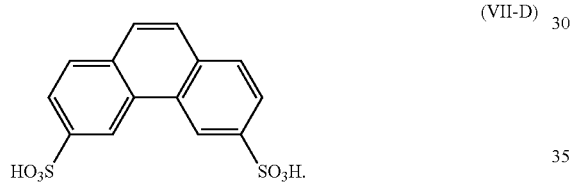

(VII-D)

23. The process of claim 1 wherein the mixture comprises one or more, natural or recombinant, antibody or a mixture of any two or more such antibodies.

24. The process of claim 1 wherein the mixture comprises one or more, natural or recombinant, enzyme or a mixture of any two or more such enzymes.

25. The process of claim 1 wherein the mixture comprises one or more, natural or recombinant, protein and/or polypeptide for diagnostic use, or a mixture of any two or more such protein and/or polypeptide.

26. The process of claim 1 wherein the mixture comprises one or more, natural or recombinant, protein or polypeptide for human or veterinary therapeutic use, or a mixture of any two or more such protein and/or polypeptide.

27. The process of claim 1 wherein the mixture comprises one or more protein or polypeptide derived from one or more, natural or recombinant, animal or human blood plasma or a mixture of any two or more such protein and/or polypeptide.

28. The process of claim 1 wherein the mixture comprises one or more protein or polypeptide derived from one or more, natural or recombinant, plant material, or a mixture of any two or more such protein and/or polypeptide.

29. The process of claim 1 wherein the mixture comprises one or more protein or polypeptide derived from one or more of animal or human milk or milk derived from a recombinant animal, or a mixture of any two or more such protein and/or polypeptide.

30. The process of claim 1 wherein the mixture comprises one or more protein or polypeptide derived from one or more, natural or recombinant, avian egg, or a mixture of any two or more such protein and/or polypeptide.

31. The process of claim 1 wherein the mixture comprises one or more protein or polypeptide derived from one or more, natural or recombinant, bacterium, yeast, fungus, virus or insect, or a mixture of any two or more such protein and/or polypeptide.

32. The process of claim 1 wherein the mixture comprises one or more protein or polypeptide derived from one or more, natural or recombinant, mammalian cell culture or animal tissue, or a mixture of any two or more such protein and/or polypeptide.

33. The process of claim 1 wherein the mixture comprises one or more organic compound, drug or drug intermediate, or a mixture of any two or more thereof.

34. The process of claim 33 wherein one or more of the one or more organic compound, drug or drug intermediate is chiral.

35. The process of claim 1 wherein in (a) x=2 or 3.

36. The process of claim 1 wherein at least one G is hydroxy and is in a position ortho to at least one An⁻.

37. A displacement chromatography process, comprising:
loading onto a stationary phase comprising an anion-exchange material a mixture comprising one or more component to be separated;
displacing at least one of the one or more component from the stationary phase by applying to the stationary phase a mixture comprising a polyaromatic polyanionic displacer compound; and
regenerating the stationary phase,
wherein the polyaromatic polyanionic displacer compound has the general formula:

Cen(Ar)$_w$ wherein Cen=a bond, an alkenyl group, an alkynyl group, a benzene ring, a biphenylene, a naphthylene, or

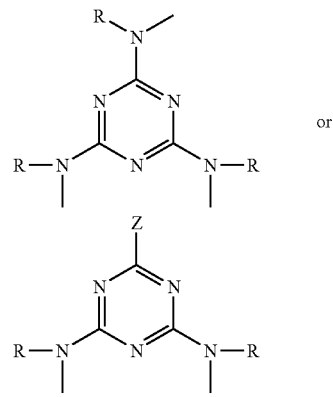

or wherein:
R=independently —H, $C_1$-$C_4$ alkyl, or $C_1$-$C_4$ hydroxyalkyl;
Z=independently —H, halogen, —OH, —OR, —NRCH$_2$CH(OH)CH$_2$OH, —NR$_2$, —N[CH$_2$CH(OH)CH$_2$OH]$_2$, —NRC(CH$_2$OH)$_3$, —NRCH(CH$_2$OH)$_2$, or —N(R)(poly(alkylene oxide));

w=2 to the highest number of substitutable positions on Cen; and

Ar=(a), (b) and/or (c); and wherein, in the following (a), (b) and (c):

An⁻=independently sulfonate, carboxylate, phosphonate, phosphinate, phosphate, a phosphate mono- or di-ester, sulfate, a sulfate mono-ester; or boronate, provided that at least one An⁻ is carboxylate;

G=H or hydroxy, with the proviso that at least one G is a hydroxy in a position ortho to the at least one carboxylate; and (a), (b) and (c) are:

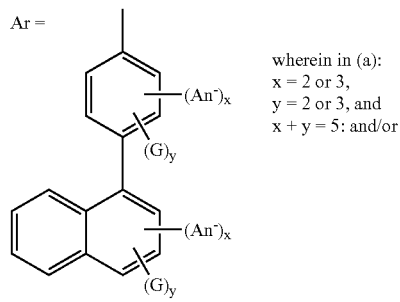

wherein in (a):
$x = 2$ or $3$,
$y = 2$ or $3$, and
$x + y = 5$: and/or or

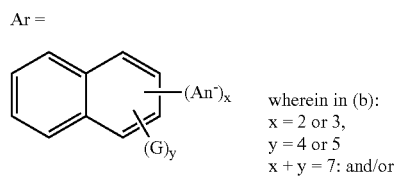

wherein in (b):
$x = 2$ or $3$,
$y = 4$ or $5$
$x + y = 7$: and/or

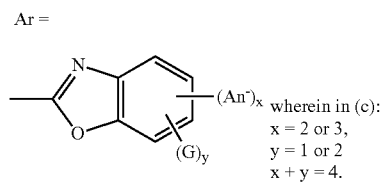

wherein in (c):
$x = 2$ or $3$,
$y = 1$ or $2$
$x + y = 4$.

38. The process of claim 37 wherein the polyaromatic polyanionic displacer compound has formula (II-A):

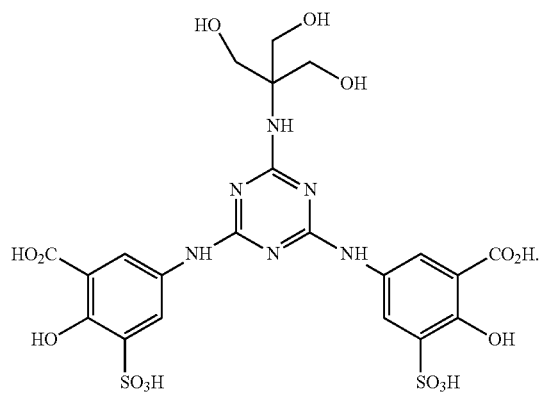

(II-A)

39. The process of claim 37 wherein the displacer compound has the following formula (III-B):

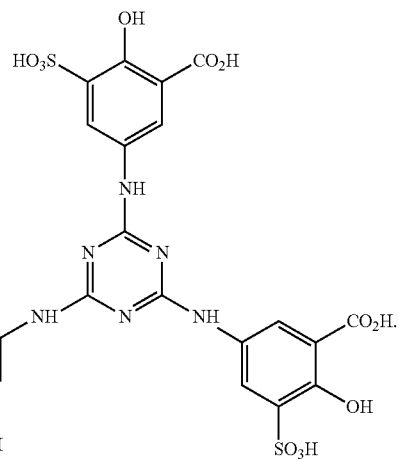

(III-B)

40. The process of claim 37 wherein Cen is a benzene ring, w=3 and Ar=(a).

41. The process of claim 37 wherein Cen is a bond, w=2 and Ar=(a).

42. The process of claim 37 wherein Cen is an alkenyl group, w=4 and Ar=(a).

43. The process of claim 37 wherein Cen is

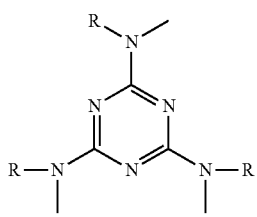

w=3, Ar=(a).

44. The process of claim 37 wherein the polyaromatic polyanionic displacer compound has the formula:

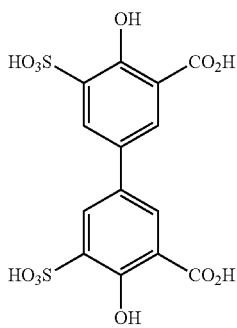 [SMILES: O=C(O)c1cc(-c2cc(C(=O)O)c(O)c(S(=O)(=O)O)c2)cc(S(=O)(=O)O)c1O]

45. The process of claim 37 wherein the polyaromatic polyanionic displacer compound has the formula:
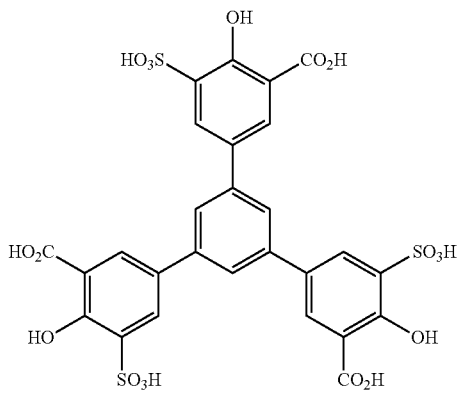 [SMILES: O=C(O)c1cc(-c2cc(-c3cc(C(=O)O)c(O)c(S(=O)(=O)O)c3)cc(-c3cc(C(=O)O)c(O)c(S(=O)(=O)O)c3)c2)cc(S(=O)(=O)O)c1O]
46. The process of claim 37 wherein the polyaromatic polyanionic displacer compound has the formula:
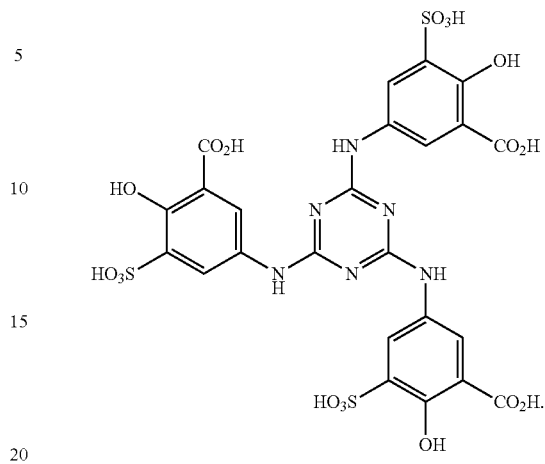
* * * * *